United States Patent
Murphy et al.

(10) Patent No.: US 10,745,739 B2
(45) Date of Patent: Aug. 18, 2020

(54) ENHANCED THROUGHPUT MINERAL COATINGS FOR OPTIMIZATION OF STEM CELL BEHAVIOR

(71) Applicant: Wisconsin Alumni Research Foundation, Madison, WI (US)

(72) Inventors: William L. Murphy, Waunakee, WI (US); Siyoung Choi, Ithaca, NY (US); Xiaohua Yu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 243 days.

(21) Appl. No.: 15/918,357

(22) Filed: Mar. 12, 2018

(65) Prior Publication Data
US 2018/0201972 A1 Jul. 19, 2018

Related U.S. Application Data

(62) Division of application No. 13/769,993, filed on Feb. 19, 2013, now Pat. No. 9,951,374.

(51) Int. Cl.
*C12Q 1/68* (2018.01)
*C12N 15/87* (2006.01)

(52) U.S. Cl.
CPC ............... *C12Q 1/68* (2013.01); *C12N 15/87* (2013.01)

(58) Field of Classification Search
CPC .................................. C12N 15/87; C12Q 1/68
USPC .......................................................... 506/10
See application file for complete search history.

(56) References Cited

U.S. PATENT DOCUMENTS

| | | | |
|---|---|---|---|
| 6,143,037 | A | 11/2000 | Goldstein et al. |
| 2005/0136438 | A1 | 6/2005 | Ralph et al. |
| 2008/0025958 | A1 | 1/2008 | Hannon et al. |
| 2008/0286361 | A1 | 11/2008 | Dobson et al. |
| 2012/0058917 | A1 | 5/2012 | Gaken et al. |
| 2013/0164270 | A1 | 6/2013 | Keshet et al. |

OTHER PUBLICATIONS

Jang et al. (J Biomed Mater Res A, Apr. 2006, 77(1), pp. 50-58) (Year: 2006).*
Aza et al., Bioceramics-simulated body fluid interfaces: pH and its influence of hydroxyapatite formation; J. Mater. Sci.; Mater. Med., 1996, vol. 7, pp. 399-402.
Barrere et al., In vitro and in vivo degradation of biomimetic octacalcium phosphate and carbonate apatite coatings on titanium implants; 2003, J. Biomed. Mater. Res. A, vol. 64, pp. 378-387.
Barrere et al., Influence of ionic strength and carbonate on the Ca-P coating formation from SBFx5 solution; 2002, Biomaterials, vol. 23, pp. 1921-1930.
Chen et al., Morphology and adhesion of mesenchymal stem cells on PLLA, apatite and apatite/collagen surfaces; 2008, J. Mater. Sci.: Mater. Med., vol. 19, pp. 2563-2567.
Choi et al., Sustained plasmid DNA release from dissolving mineral coatings, Acta Biomater.; 2010, vol. 6, pp. 3426-3435.
Choosakoonkriang et al., Biophysical characterization of PEI/DNA complexes; 2003, J. Pharm. Sci., vol. 92, pp. 1710-1722.
Chou et al., The effect of pH on the structural evolution of accelerated biomimetic apatite; 2004, Biomaterials, vol. 25, pp. 5323-5331.
Chowdhury et al., Fluoride enhances transfection activity of carbonate apatite by increasing cytoplasmic stability of plasmid DNA, Biochemical and Biophysical Research Communications, 2011, vol. 409, pp. 745-747.
Gerasimenko et al., Calcium uptake via endocytosis with rapid release from acidifying endosomes; 1998, Curr. Biol., vol. 8, pp. 1335-1338.
Haberland et al., Calcium ions as efficient cofactor of polycation-mediated gene transfer; 1999, Biochim. Blophys. Acta, vol. 1445, pp. 21-30.
Jalota et al., Effect of carbonate content and buffer type on calcium phosphate formation in SBF solutions; 2006, J. Mater. Sci.: Mater. Med., vol. 17, pp. 697-707.
Jewell et al., Multilayered polyelectrolyte films promote the direct and localized delivery of DNA to cells; 2005, J. Controlled Release, vol. 106, pp. 214-223.
Jordan et al., Transfecting mammalian cells: optimization of critical parameters affecting calcium-phosphate precipitate formation, Nucleic Acids Res.; 1996, vol. 24, pp. 596-601.
Jongpaiboonkit et al., Mineral-coated polymer microspheres for controlled protein binding and release; 2009, Adv. Mater., vol. 21, pp. 1960-1963.
Kulkarni et al., Role of calcium in gene delivery; 2006, Expert Opin. Drug Del iv., vol. 3, pp. 235-245.
Lam et al., Calcium enhances the transfection potency of plasmid DNA-cationic liposome complexes; 2000, Biochim. Blophys. Acta, vol. 1463, pp. 279-290.
Leonova et al., Substrate mineralization stimulates focal adhesion contact redistribution and cell motility of bone marrow stromal cells; 2006, J. Biomed. Mater. Res. A, vol. 79, pp. 263-270.
Lin et al., Study of hydroxyapatite osteoinductivity with an osteogenic differentiation of mesenchymal stem cells; 2009, J. Biomed. Mater. Res. A, vol. 89, pp. 326-335.

(Continued)

*Primary Examiner* — Karla A Dines
(74) *Attorney, Agent, or Firm* — Stinson LLP

(57) ABSTRACT

Disclosed are methods for cell transfection and regulating cellular behavior. More particularly, the present disclosure relates to methods of non-viral cell transfection and regulating cellular behavior using mineral coatings that allow for the enhanced transfection of cells. The mineral coatings bind polynucleotides and provide a source of calcium and phosphate ions to enhance transfection. The present disclosure also provides a high throughput platform for screening non-viral transfection of cells. The methods of the present disclosure also provide an advantageous polynucleotide delivery platform because the mineral coatings may be deposited on various medical device materials after being specifically developed using the high throughput screening platform.

10 Claims, 22 Drawing Sheets

(56) References Cited

OTHER PUBLICATIONS

Luong et al., Gene delivery via DNA incorporation within a biomimetic apatite coating; 2009, Biomaterials, vol. 30, pp. 6996-7004.
Matsumoto et al., Hydroxyapatite particles as a controoled release carrier of protein; 2004, Biomaterials, vol. 25, pp. 3807-3812.
Müller et al., Calcium phosphate surfaces promote osteogenic differentiation of mesenchymal stem cells; 2008, J. Cell. Mol. Med., vol. 12, pp. 281-291.
Müller et al., Preparation of SBF with different HC03-content and its influence on the composition of biomimetic apatites; 2006, Acta Biomater., vol. 2, pp. 181-189.
Murphy et al., Effects of bone-like mineral film on phenotype of adult human mesenchymal stem cells in vitro; 2005, Biomaterials, vol. 26, pp. 303-310.
Pannier et al., Surface polyethylene glycol enhances substrate-mediated gene delivery by nonspecifically immobilized complexes; 2008, Acta Biomater., vol. 4, pp. 26-39.
Qu, et al., The effect of temperature and initial pH on biomimetic apatite coating; 2008, J. Biomed. Mater. Res. B, vol. 87, pp. 204-212.
Richard et al., Behavior of human osteoblast-like cells in contact with electrodeposited calcium phosphate coatings; 2006, J. Biomed. Mater. Res. B, vol. 79, pp. 108-115.
Sandhu et al., Calcium enhances the transfection potency of stabilized plasmid-lipid particles; 2005, Anal. Biochem., vol. 341, pp. 156-164.
Shen et al., Surface-mediated gene transfer from nanocomposites of controlled texture; 2004, Nat. Mater., vol. 3, pp. 569-574.
Shu et al., Hydroxyapatite accelerates differentiation and suppresses growth of MC3T3-E1 osteoblasts; 2003, J. Biomed. Mater. Res. A, vol. 15, pp. 1196-1204.
Xu et al., Mechanism of DNA release from cationic liposome/DNA complexes used in cell transfection; 1996, Biochem. vol. 35, pp. 5616-5623.
Zaitsev et al., Histon H1-mediated transfection: role of calcium in the cellular uptake and intracellular fate of H1-DNA complexes; 2002, Acta Histochem., vol. 104, pp. 85-92.
Zhu et al., The effect of surface charge on hydroxyapatite nucleation; 2004, Biomaterials, vol. 25, pp. 3915-3921.
Jang et al., Surface adsorption of DNA to tissue engineering scaffolds for efficient gene delivery; 2006, Journal of Biomedical Materials Research Part A, vol. 77A, No. 1, pp. 50-58.
Jordan et al., Transferring mammalian cells: optimization of critical parameters affecting calcium-phosphate precipitate formation; Nucleic Acids Res., 1996, vol. 24, No. 4, pp. 596-601.
Brestovitsky et al., Journal of Visualized Experiments, 2012, pp. 1-7.
Byun et al., Plasmid vectors harboring cellular promoters can induce prolonged gene expression in hematopoietic and mesenchymal progenitor cells; Biochemical and Biophysical Research Communications; 2005, vol. 332, No. 2, pp. 518-523.
Oyane et al., Calcium phosphate composite layers for surface-mediated gene transfer; 2012, Acta Biomaterialia, vol. 3, pp. 2034-2046.

* cited by examiner

FIG. 1A
FIG. 1B
2 x SBF 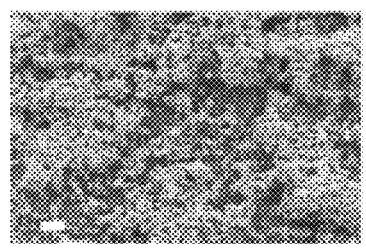 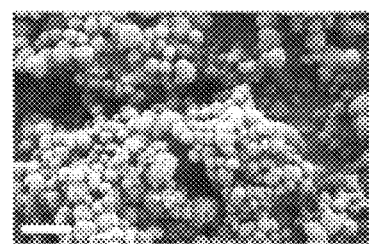
FIG. 1C
FIG. 1D
3.5 x SBF 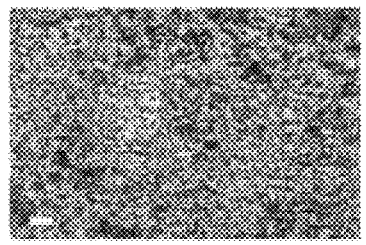 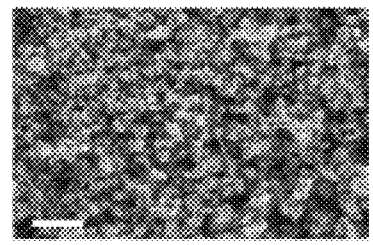
FIG. 1E
FIG. 1F
5 x SBF 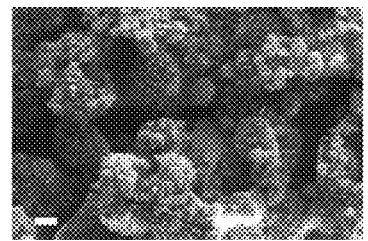 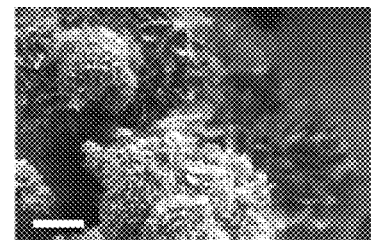

ENHANCED THROUGHPUT MINERAL COATINGS FOR OPTIMIZATION OF STEM CELL BEHAVIOR

CROSS REFERENCE TO RELATED APPLICATIONS

This application is a divisional application based on U.S. patent application Ser. No. 13/769,993 filed on Feb. 19, 2013, which is hereby incorporated by reference in its entirety.

STATEMENT OF GOVERNMENT SUPPORT

This invention was made with government support under AR052893 awarded by the National Institutes of Health. The government has certain rights in the invention.

BACKGROUND OF THE DISCLOSURE

The present disclosure relates generally to methods for cell transfection and regulating cellular behavior. More particularly, the present disclosure relates to methods of using biodegradable mineral coatings for non-viral cell transfection and regulating cellular behavior.

Transfection is the process of introducing nucleic acids into cells. Various transfection strategies are available that generally involve opening transient pores in the cell membrane to allow the uptake of material by the cell. Two broad categories of transfection include chemical-based transfection methods and non-chemical transfection methods. Chemical-based transfection methods include, for example, calcium phosphate-based transfection and liposome-based transfection. In calcium phosphate-based transfection, a buffer containing phosphate ions is combined with a calcium chloride solution containing the DNA to be transfected to form calcium-phosphate precipitates that bind DNA. A suspension of the precipitate is added to cells, which take up the precipitate and DNA. In liposome-based transfection, DNA is incorporated into liposomes that fuse with the cell membrane to release the DNA into the cells.

The deposition of calcium phosphate (CaP)-based materials on various substrates has been used to develop bioactive interfaces for studying its interaction with bone-forming cells. In addition, CaP mineral substrates bind and release biological molecules (e.g., DNA). Studies have also been conducted to investigate the role of CaP mineral properties (physical and chemical) in regulating cellular behavior, including stem cell attachment, proliferation, and differentiation. However, these previous studies have not been capable of systematically studying CaP mineral effects on stem cell proliferation and differentiation. Taken together, the potential impact of these materials on non-viral transfection and stem cell behavior as well as the inherent complexity of CaP requires novel strategies to identify useful CaP mineral coatings. Accordingly, there exists a need to develop non-viral transfection methods and systems for use with these methods.

SUMMARY OF THE DISCLOSURE

The present disclosure relates generally to methods for cell transfection and regulating cellular behavior. More particularly, the present disclosure relates to methods of non-viral cell transfection and regulating cellular behavior using mineral coatings. The methods of non-viral transfection allow for the enhanced transfection of cells. The mineral coatings bind polynucleotides and provide a source of calcium and phosphate ions for transfection of cells. The present disclosure also provides a high throughput platform for screening non-viral transfection of cells. The methods of the present disclosure also provide an advantageous polynucleotide delivery platform because the mineral coatings may be deposited on various medical device materials after the mineral coating has been specifically developed using the high throughput screening platform to determine the appropriate mineral coating for the transfection of a particular cell in a particular environment or condition.

In one aspect, the present disclosure is directed to a method of non-viral transfection. The method includes preparing a substrate comprising a mineral coating, wherein the mineral coating is formed by incubating the substrate in a simulated body fluid. The simulated body fluid comprises from about 5 mM to about 12.5 mM calcium ions, from about 2 mM to about 12.5 mM phosphate ions, from about 4 mM to about 100 mM carbonate ions, and a pH of from about 5 to about 7.5. A polynucleotide is then contacted with the substrate comprising the mineral coating, wherein the polynucleotide binds to the mineral coating. Then a cell is contacted with the mineral coating; and the cell is cultured.

In another aspect, the present disclosure is directed to a high throughput non-viral transfection system comprising a substrate comprising: a plurality of mineral coatings, wherein the plurality of mineral coatings comprises a calcium to phosphate ratio of from about 2.5:1 to about 1:1; a polynucleotide bound to the plurality of mineral coatings; and a plurality of cells.

In another aspect, the present disclosure is directed to a method of screening non-viral transfection of cells comprising: culturing a plurality of cells on a plurality of mineral coatings comprising a polynucleotide bound to the mineral coatings, wherein the mineral coatings are formed by hydrolyzing poly(α-hydroxy ester) coatings on a substrate comprising a plurality of wells; incubating the hydrolyzed poly(α-hydroxy ester) coatings in a plurality of simulated body fluids comprising a calcium ion concentration of from about 5 mM to about 12.5 mM, a phosphate ion concentration of from about 2 mM to about 12.5 mM, a carbonate ion concentration of from about 4 mM to about 100 mM, and a pH of from about 4 to about 7.5.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1F are scanning electron micrographs of calcium-phosphate mineral coatings grown on poly lactide glycolide (PLG) films in 2× simulated body fluid (SBF), 3.5×SBF and 5×SBF as discussed in Example 2.

Figure 2:
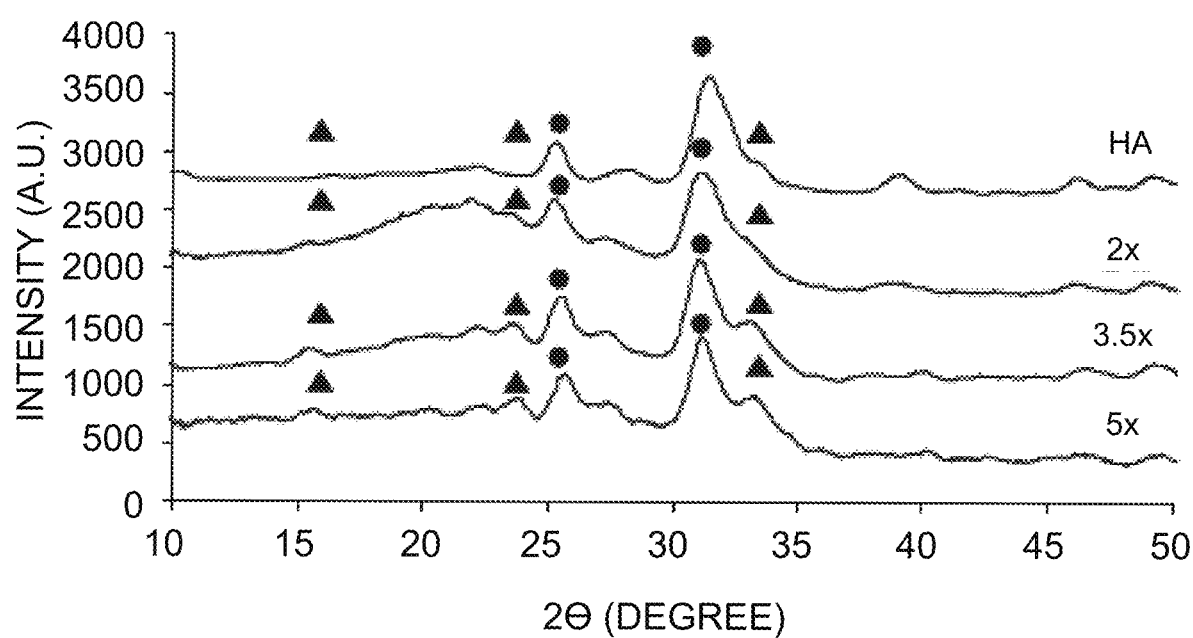
FIG. 2 shows an X-ray diffraction spectra of commercially available hydroxyapatite and calcium-phosphate mineral coatings grown on poly lactide glycolide (PLG) films in 2×SBF, 3.5×SBF and 5×SBF as discussed in Example 2.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, methods have been developed for non-viral transfection of cells. Surprisingly, use of the mineral coatings of the present disclosure for transfection showed 150-fold greater transfection rates when compared to current transfection methods. The mineral coatings bind polynucleotides and provide a source of calcium and phosphate ions to enhance transfection. The present disclosure also provides a high throughput platform for screening non-viral transfection of cells. The methods of the present disclosure also provide an advantageous polynucleotide delivery platform because the mineral coatings may be deposited on various medical device materials after being specifically developed using the high throughput screening platform.

Methods of Non-Viral Transfection

In one aspect, the present disclosure is generally directed to a method of non-viral transfection by forming a mineral coating on a substrate, wherein the mineral coating is formed by incubating the substrate in a simulated body fluid (SBF); contacting the substrate with a polynucleotide, wherein the polynucleotide binds to the mineral coating; contacting a cell with the mineral coating; and culturing the cell.

Suitable substrates on which the mineral coating may be include polymers, ceramics, metals, glass and combinations thereof in the form, for example, of particles, films, dishes, plates, coverslips and slides. Particularly suitable particles may be, for example, agarose beads, latex beads, magnetic beads, and combinations thereof. Particularly suitable dishes may be, for example, culture dishes. Particularly suitable plates may be, for example, microtiter plates having, for example, 4, 6, 14, 96, or more sample wells. Suitable substrates may be polymers, ceramics, metals, glass and combinations thereof.

The substrates may be initially coated with a poly(α-hydroxy ester) film, for example. Particularly suitable poly (α-hydroxy esters) may be, for example, poly(L-lactide), poly(lactide-co-glycolide), poly(ε-caprolactone), and combinations thereof. It should be understood that when making any combinations of the above films, the films are typically mixed in suitable organic solvents as known in the art. Further, differences in molecular weights, crystallization rates, glass transition temperatures, viscosities, and the like should be taken into consideration as well as understood in the art to prevent phase separation and lack of uniformity in the final substrates. Phase separation and lack of uniformity can further be avoided by altering the mixing ratio of the films used in the substrate.

After preparing a poly(α-hydroxy ester) film on the substrate, the surface of the film coating is hydrolyzed under alkaline conditions to create a surface having COOH and OH groups. After surface hydrolyzing, the substrate is incubated in a simulated body fluid containing a suitable mineral-forming material to form a mineral coating. Suitable mineral-forming materials may be, for example, calcium, phosphate, carbonate, and combinations thereof.

The simulated body fluid (SBF) for use in the methods of the present disclosure typically includes from about 5 mM to about 12.5 mM calcium ions, including from about 7 mM to about 10 mM calcium ions, and including about 8.75 mM calcium ions; from about 2 mM to about 12.5 mM phosphate ions, including from about 2.5 mM to about 7 mM phosphate ions, and including from about 3.5 mM to about 5 mM phosphate ions; and from about 4 mM to about 100 mM carbonate ions.

In some embodiments, the SBF may further include about 145 mM sodium ions, from about 6 mM to about 9 mM potassium ions, about 1.5 mM magnesium ions, from about 150 mM to about 175 mM chloride ions, about 4 mM $HCO_3^-$, and about 0.5 mM $SO_4^{2-}$ ions.

The pH of the SBF may typically range from about 4 to about 7.5, including from about 5.3 to about 6.8, including from about 5.7 to about 6.2, and including from about 5.8 to about 6.1.

Suitable SBF may include, for example: about 145 mM sodium ions, about 6 mM to about 9 mM potassium ions, about 5 mM to about 12.5 mM calcium ions, about 1.5 mM magnesium ions, about 150 mM to about 175 mM chloride ions, about 4.2 mM $HCO_3^-$, about 2 mM to about 5 mM $HPO_4^{2-}$ ions, and about 0.5 mM $SO_4^{2-}$ ions. The pH of the simulated body fluid may be from about 5.3 to about 7.5, including from about 6 to about 6.8.

In one embodiment, the SBF may include, for example: about 145 mM sodium ions, about 6 mM to about 17 mM potassium ions, about 5 mM to about 12.5 mM calcium ions, about 1.5 mM magnesium ions, about 150 mM to about 175 mM chloride ions, about 4.2 mM to about 100 mM $HCO_3^-$, about 2 mM to about 12.5 mM phosphate ions, and about 0.5 mM $SO_4^{2-}$ ions. The pH of the simulated body fluid may be from about 5.3 to about 7.5, including from about 5.3 to about 6.8.

In another embodiment, the SBF includes: about 145 mM sodium ions, about 6 mM to about 9 mM potassium ions, from about 5 mM to about 12.5 mM calcium ions, about 1.5 mM magnesium ions, about 60 mM to about 175 mM chloride ions, about 4.2 mM to about 100 mM $HCO_3^-$, about 2 mM to about 5 phosphate ions, about 0.5 mM $SO_4^{2-}$ ions, and a pH of from about 5.8 to about 6.8, including from about 6.2 to about 6.8.

In yet another embodiment, the SBF includes: about 145 mM sodium ions, about 9 mM potassium ions, about 12.5 mM calcium ions, about 1.5 mM magnesium ions, about 172 mM chloride ions, about 4.2 mM $HCO_3^-$, about 5 mM to about 12.5 mM phosphate ions, about 0.5 mM $SO_4^{2-}$ ions, from about 4 mM to about 100 mM $CO_3^{2-}$, and a pH of from about 5.3 to about 6.0.

The mineral coatings may be formed by incubating the substrate with the SBF at a temperature of about 37° C. for a period of time of from about 3 days to about 10 days.

After completion of the mineral coating preparation, the mineral coatings may be analyzed to determine the morphology and composition of the mineral coatings. The composition of the mineral coatings may be analyzed by energy dispersive X-ray spectroscopy, Fourier transform infrared spectrometry, X-ray diffractometry, and combinations thereof. Suitable X-ray diffractometry peaks may be, for example, at 26° and 31°, which correspond to the (0 0 2) plane, the (2 1 1) plane, the (1 1 2) plane, and the (2 0 2) plane for the hydroxyapatite mineral phase. Particularly suitable X-ray diffractometry peaks may be, for example, at 26° and 31°, which correspond to the (0 0 2) plane, the (1 1 2) plane, and the (3 0 0) plane for carbonate-substituted hydroxyapatite. Other suitable X-ray diffractometry peaks may be, for example, at 16°, 24°, and 33°, which correspond to the octacalcium phosphate mineral phase. Suitable spectra obtained by Fourier transform infrared spectrometry analysis may be, for example, a peak at 450-600 $cm^{-1}$, which corresponds to O—P—O bending, and a peak at 900-1200 $cm^{-1}$, which corresponds to asymmetric P—O stretch of the $PO_4^{3-}$ group of hydroxyapatite. Particularly suitable spectra peaks obtained by Fourier transform infrared spectrometry analysis may be, for example, peaks at 876 $cm^{-1}$, 1427 $cm^{-1}$, and 1483 $cm^{-1}$, which correspond to the carbonate ($CO_3^{2-}$) group. The peak for $HPO_4^{2-}$ may be influenced by adjusting the calcium and phosphate ion concentrations of the SBF used to prepare the mineral coating. For example, the $HPO_4^{2-}$ peak may be increased by increasing the calcium and phosphate concentrations of the SBF. Alternatively, the $HPO_4^{2-}$ peak may be decreased by decreasing the calcium and phosphate concentrations of the SBF. Another suitable peak obtained by Fourier transform infrared spectrometry analysis may be, for example, a peak obtained for the octacalcium phosphate mineral phase at 1075 $cm^{-1}$, which may be influenced by adjusting the calcium and phosphate ion concentrations in the simulated body fluid used to prepare the mineral coating. For example, the 1075 $cm^{-1}$ peak may be made more distinct by increasing the calcium and phosphate ion concentrations in the simulated body fluid used to prepare the mineral coating. Alternatively, the 1075 $cm^{-1}$ peak may be made less distinct by decreasing the calcium and phosphate ion concentrations in the simulated body fluid used to prepare the mineral coating.

Energy dispersive X-ray spectroscopy analysis may also be used to determine the calcium/phosphate ratio of the mineral coating. For example, the calcium/phosphate ratio may be increased by decreasing the calcium and phosphate ion concentrations in the SBF. Alternatively, the calcium/phosphate ratio may be decreased by increasing the calcium and phosphate ion concentrations in the SBF. Analysis of the mineral coatings by energy dispersive X-ray spectroscopy allows for determining the level of carbonate ($CO_3^{2-}$) substitution for $PO_4^{3-}$ and incorporation of $HPO_4^{2-}$ into the mineral coatings. Typically, the SBF includes calcium and phosphate ions in a ratio of from about 10:1 to about 0.2:1, including from about 2.5:1 to about 1:1.

Further, the morphology of the mineral coatings may be analyzed by scanning electron microscopy, for example. Scanning electron microscopy may be used to visualize the morphology of the resulting mineral coatings. The morphology of the resulting mineral coatings may be, for example, a spherulitic microstructure, plate-like microstructure, and/or a net-like microstructure. Suitable average diameters of the spherulites of a spherulitic microstructure may be, for example, from about 2 μm to about 42 μm. Particularly suitable average diameters of the spherulites of a spherulitic microstructure may be, for example, from about 2 μm to about 4 μm. In another embodiment, particularly suitable average diameters of the spherulites of a spherulitic microstructure may be, for example, from about 2.5 μm to about 4.5 μm. In another embodiment, particularly suitable average diameters of the spherulites of a spherulitic microstructure may be, for example, from about 16 μm to about 42 μm.

The method further includes contacting a polynucleotide with the mineral coating. The polynucleotide may be contacted with the mineral coating using any method known in the art. For example, a solution of the polynucleotide may be pipetted, poured, or sprayed onto the mineral coating. Alternatively the mineral coating may be dipped in a polynucleotide solution. The polynucleotide binds to the mineral coating by an electrostatic interaction between the polynucleotide and the mineral coating.

Any polynucleotide may be contacted with the mineral coating for use in the method of non-viral transfection. Suitable polynucleotides may be, for example, plasmids, oligonucleotides, small interfering RNAs (siRNAs), messenger RNA (mRNA), short hairpin RNAs (shRNAs), DNA aptamers, and RNA aptamers.

The polynucleotides may encode any protein of interest. For example, the polynucleotides may encode proteins including growth factors and reporters. Particularly suitable proteins may be, for example, proteins involved in the growth and the repair of bone such as, for example, BMP1, BMP2, BMP3, BMP4, BMP5, BMP6, BMP7, BMP8a, EGF, PDGFA, PDGFB, PDGFC, PDGFD, PDGFAB, VEGF-A, placenta growth factor (PlGF), VEGF-B, VEGF-C, VEGF-D, TGF-β1, TGF-β2, TGF-β3, AMH, ARTN, GDF1, GDF2, GDF3, GDF3A, GDF5, GDF6, GDF7, GDF8, GDF9, GDF10, GDF11, GDF15, GDFN, INHA, INHBA, INHBB, INHBC, INHBE, LEFTY1, LEFTY2, MSTN, NODAL, NRTN, PSPN, FGF1, FGF2, FGF3, FGF4, CBFA1/RUNX2, OSTERIZ, and SOX9. Suitable reporters may be, for example, green fluorescent protein, chloramphenicol acetyltrasferase, β-galactosidase, β-glucuronidase, and luciferase.

The method further includes contacting a cell with the mineral coating having a polynucleotide and culturing the cell. Contacting the cell includes seeding the cell to be transfected on the mineral coating having the polynucleotide. The cells are contacted with the mineral coating by adding a solution containing cells to the mineral coating and allowing cells in the solution to settle onto the mineral coating. Cells may be seeded, for example, at a density of from about $2.4 \times 10^4$ cells/cm$^2$ to about $7.2 \times 10^4$ cells/cm$^2$.

As the cells contact the mineral coating, the cells may change shape and form adhesions with the mineral coating. The cells may also migrate on the mineral layer. Those skilled in the art will appreciate that, like any cell culture system, the non-viral mineral coating is not a static system.

After seeding, the cells are cultured on the mineral layer for any suitable period of time. The suitable period of time may be for a period of time such that the cells reach a particular confluence. For example, a suitable confluence may be from about 20% confluence to about 100% confluence. A particularly suitable confluence may be about 30% confluence. Those skilled in the art can determine the suitable amount of confluence for the particular cell type by determining the desired percent confluence at various percent confluence while culturing the cells up to about 100% confluence.

The method may include culturing the cells on the mineral coating having the polynucleotide with a polynucleotide release medium typically including calcium ions, phosphate ions, or a combination thereof. Culturing the cells in the polynucleotide release medium may allow for the sustained release of the polynucleotide from the mineral coating and make it available for transfection of the cell. The polynucleotide release medium may also cause the dissolution of the mineral layer such that calcium and phosphate ions are released from the mineral coating and made available for transfection of the cell.

Suitable ion concentration of the polynucleotide release medium may be from about 0 mM calcium chloride to about 2.5 mM calcium chloride and from about 0 mM potassium phosphate to about 1 mM potassium phosphate. Suitable pH of the polynucleotide-release medium may be, for example, from about 6.2 to about 7.8, including from about 7.2 to about 7.4.

Particularly suitable polynucleotide-release media may have, for example, from about 0 mM calcium chloride to about 1.5 mM calcium chloride, from about 0 mM potassium phosphate to about 0.6 mM potassium phosphate, and a pH of from about 4 to about 6.5. Without being bound by theory, calcium and phosphate ions may influence polynucleotide uptake and endosomal escape, leading to enhanced non-viral transfection. The calcium and phosphate ions may form calcium-phosphate nanoparticles near the dissolving mineral coating, which may enhance non-viral transfection of the cells cultured on the mineral coatings.

High Throughput Platforms for Non-Viral Transfection

In another embodiment, the present disclosure is directed to a high throughput platform for non-viral transfection. The high throughput platform includes a substrate having a plurality of mineral coatings and a polynucleotide. Suitable substrates may be any type of plate or dish with more than one well or chamber that allows for the comparison between the wells or chambers. Particularly suitable substrates may be, for example, multiwell plates, multi-chambered plates, multiwell dishes, multiwell slides, and multiwell arrays such as those having, for example, 6-, 12-, 24-, 48-, 96-, or more wells, chambers or arrays.

The substrates include the substrates previously described and may be manufactured from a variety of materials. Suitable materials may be, for example, polystyrene, polypropylene, polycarbonate, cycloolefins, glass, and combinations thereof.

A plurality of mineral coatings as described herein may be prepared according to the number of wells, chambers, and arrays contained on the substrates.

A polynucleotide is then contacted with the mineral coatings to bind the polynucleotide to the mineral coating, as described herein. The amount of polynucleotide bound to the mineral coating may be controlled by controlling the morphology of the mineral coating. For example, polynucleotide binding to the mineral coating may be increased by decreasing the calcium and phosphate in the SBF used to prepare the mineral coating. Alternatively, polynucleotide binding to the mineral coating may be decreased by increasing the calcium and phosphate in the SBF used to prepare the mineral coating.

After the polynucleotide is bound to the mineral coatings, cells may be seeded on the mineral coating, as described herein. Any suitable cell type may be cultured on the mineral coatings. Particularly suitable cell types may be, for example, pluripotent stem cells, mesenchymal stem cells, and umbilical vein endothelial cells.

Cells may be cultured on the mineral coatings for any desired period of time. Suitable time may be, for example, from less than 1 day to about 3 weeks. Suitable times may be determined by those skilled in the art using well known methods. For example, cells may be cultured for a time sufficient to reach a desired confluence. Cells may be cultured for a time sufficient to reach a desired level of transfection as determined by detecting the expression level of the polynucleotide, detecting the presence or absence of a marker, and conducting an enzyme assay, for example.

Methods of Screening Non-Viral Transfection

In another aspect, the present disclosure is directed to a method of screening non-viral transfection of cells. The method includes culturing a plurality of cells on a plurality of mineral coatings comprising a polynucleotide bound to the mineral coatings, wherein the mineral coatings are formed by hydrolyzing poly(α-hydroxy ester) coatings on a substrate comprising a plurality of wells; incubating the hydrolyzed poly(α-hydroxy ester) coatings in a plurality of simulated body fluids comprising a calcium ion concentration of from about 5 mM to about 12.5 mM, a phosphate ion concentration of from about 2 mM to about 12.5 mM, a carbonate ion concentration of from about 4 mM to about 100 mM, a calcium to phosphate ratio of from about 2.5:1 to about 1:1, and a pH of from about 4 to about 7.5.

The method may further include analyzing transfection of the cells. Transfection may be analyzed using methods known by those skilled in the art. Suitable methods may be, for example, luminescence, fluorescence, enzyme linked immunosorbent assay (ELISA), Western blot analysis, Northern blot analysis, Southern blot analysis, polymerase chain reaction, and microscopy.

The disclosure will be more fully understood upon consideration of the following non-limiting Examples.

EXAMPLES

Example 1

Preparation of Mineralized Coatings on PLG Film

In this Example, mineral coatings were prepared on poly lactide glycolide (PLG) film.

Specifically, poly (lactide-co-glycolide) ("PLG") (lactide: glycolide 85:15, average molecular weight 50,000-70,000) was purchased from Sigma-Aldrich (St. Louis, Mo.). PLG was dissolved in chloroform and dried to make 1 cm×1 cm PLG films. PLG film was surface hydrolyzed in 1 M NaOH solution for 1 hour to create a surface having COOH and OH groups and rinsed in deionized (DI) water (18 MΩ cm). Various mineral solutions were prepared by dissolving NaCl, KCl, MgSO$_4$, MgCl$_2$, NaHCO$_3$, CaCl$_2$, KH$_2$PO$_4$ and Tris base in DI water and adjusting the pH by adding HCl and NaOH for the supersaturated mineral solutions. Ion concentrations and pH values of the various mineral solutions are listed in Table 1 below. Mineral coatings were formed on PLG films by incubating the PLG films in the various mineral solutions at 37° C. for 10 days. The mineral solutions were refreshed daily and the resulting mineral-coated PLG films were rinsed in DI water and freeze dried until use.

TABLE 1

Ion Concentrations and pH Values of Mineral Solutions

| | Concentration (mM) | | | | | | | | |
|---|---|---|---|---|---|---|---|---|---|
| | Na$^+$ | K$^+$ | Ca$^{2+}$ | Mg$^{2+}$ | Cl$^-$ | HCO$_3^-$ | HPO$_4^{2-}$ | SO$_4^{2-}$ | pH |
| Blood Plasma | 142.0 | 5.0 | 2.5 | 1.5 | 103.0 | 27.0 | 1.0 | 0.5 | 7.4 |
| 2X SBF | 145.2 | 6.0 | 5.0 | 1.5 | 157 | 4.2 | 2.0 | 0.5 | 6.8 |
| 3.5X SBF | 145.2 | 7.5 | 8.75 | 1.5 | 164.5 | 4.2 | 3.5 | 0.5 | 6.3 |
| 5X SBF | 145.2 | 9.0 | 12.5 | 1.5 | 172 | 4.2 | 5.0 | 0.5 | 6.0 |

Example 2

Characterization of Mineral Coatings on PLG Films

In this Example, the mineral coatings on PLG films were characterized.

Specifically, the morphology of mineral coatings on PLG films was examined by scanning electron microscopy (SEM) (Carl Zeiss STM model LEO-1530) operating at 5 keV. Mineral coated PLG films were sputter coated with gold using a sputter coater (Denton Vacuum model DESK II) under 50 mTorr pressure, 40 mA current and a 35-second coating time. To characterize the mineral composition, energy dispersive X-ray spectroscopy (EDS) analysis was performed in conjunction with SEM. A Fourier transform infrared (FTIR) spectrometer (Bruker model EQUINOX 55) was used for further compositional analysis. Mineral coatings were scraped from the PLG films, mixed with potassium bromide, pressed into a pellet and analyzed. All FTIR spectra were recorded in the range of 400-2000 cm$^{-1}$. Hydroxyapatite powders (Sigma-Aldrich, St. Louis, Mo.) were used as a reference material. The crystal phases of mineral coatings on PLG films were analyzed using X-ray diffractometry (XRD) (Bruker AXS model HI-STAR). The mineral coatings scraped from PLG films were mounted using glass number 50 capillary tubes (Hampton Research, Aliso Viejo, Calif.) and analyzed under Cu Kα radiation. XRD spectra were taken for 10 minute scanning in the range 2Θ=10-50°.

Figure 3:
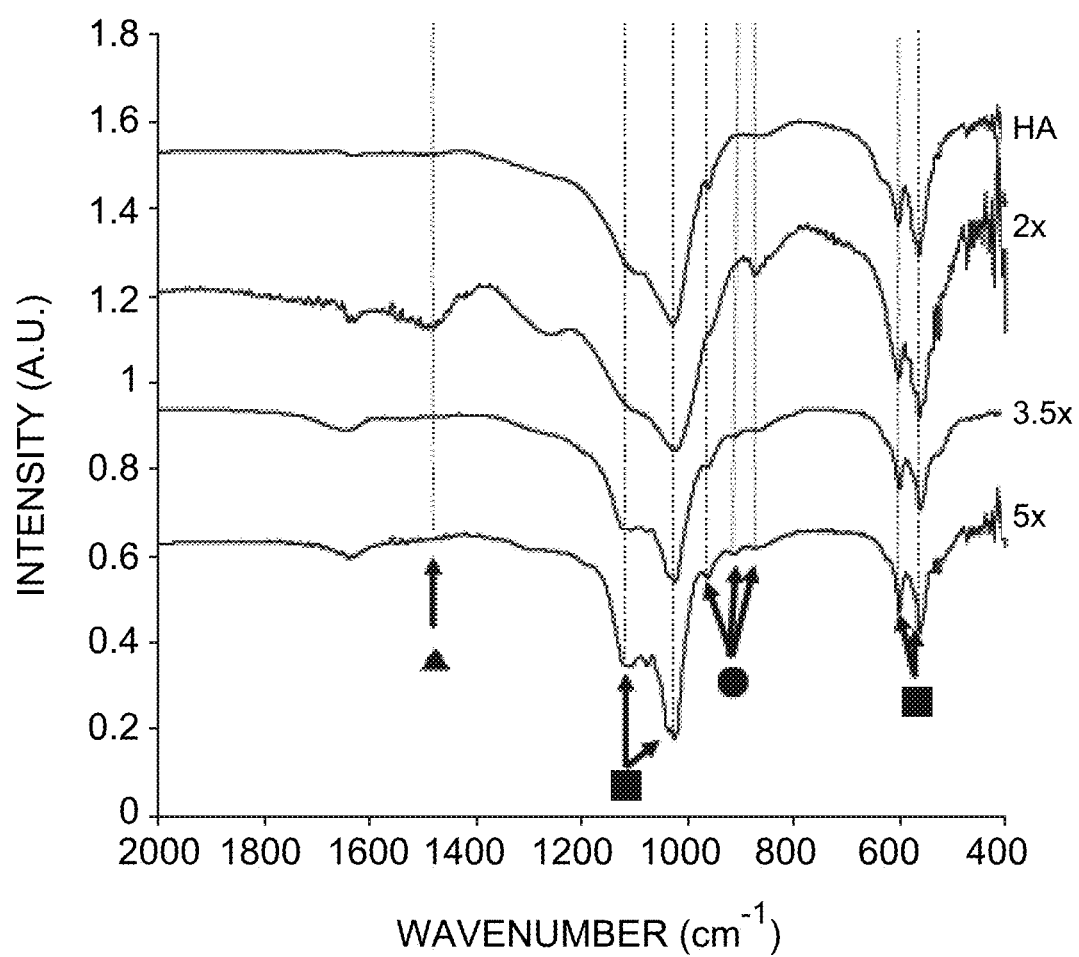
FIG. 3 shows a Fourier transform infrared (FTIR) spectra of commercially available hydroxyapatite and calcium-phosphate mineral coatings grown on poly lactide glycolide (PLG) films in 2×SBF, 3.5×SBF and 5×SBF as discussed in Example 2.

The morphology of mineral coatings formed on PLG films was influenced by the calcium and phosphate ion concentrations, as well as pH of the simulated body fluid. As shown in FIGS. 1A-1F, mineral coatings in all simulated body fluid conditions had a spherulitic microstructure and plate-like nanostructure. The average diameter of mineral spherulites formed in 2×SBF (3.1±0.92 μm) and 3.5×SBF (3.5±0.9 μm) were significantly smaller than mineral spherulites formed in 5×SBF (28.9±12.37 μm). The calcium and phosphate ion concentrations and the pH in SBF solution influenced both the phase (see, FIG. 2) and the composition (see, FIG. 3) of the mineral coatings. The appearance of two main X-ray diffraction peaks at 26° and 31° indicated that the mineral coatings were primarily composed of a hydroxyapatite mineral phase. The 26° peak corresponds to the (0 0 2) plane of hydroxyapatite and the 31° peak corresponds to the (2 1 1), (1 1 2) and (2 0 2) planes. Carbonate-substituted hydroxyapatite has also been shown to display peaks at 26° and 31°, which correspond to the (0 0 2) plane and the (1 1 2) and (3 0 0) planes of carbonate-substituted hydroxyapatite. Thus, the XRD spectra were consistent with carbonate substitution in the hydroxyapatite mineral. Spectra from FTIR analysis showed two dominant peaks that could be attributed to O—P—O bending and asymmetric P—O stretch of the $PO_4^{3-}$ group of hydroxyapatite (see FIG. 3). Vibration peaks at 876, 1427 and 1483 cm-1, which could be assigned to the carbonate ($CO_3^{2-}$) group, were more strongly detected in mineral coatings formed in 2×SBF when compared with those in 3.5× and 5×SBF. Thus, this result indicated that carbonate incorporation into mineral coatings was enhanced in 2×SBF.

High calcium and phosphate ion concentrations and low pH of SBF solutions provided favorable conditions for growth of an octacalcium phosphate (OCP) mineral phase. XRD spectra showed peaks at 16°, 24° and 33°, which could be attributed to the OCP phase (see, FIG. 2). OCP peaks were more distinct when calcium and phosphate ion concentrations in SBF were increased. Significantly, the lower initial pH of 3.5×SBF (pH 6.3) and 5×SBF (pH 6.0) may have provided a more favorable environment for OCP nucleation, which resulted in enhanced OCP content in the mineral coatings. OCP is a less stable phase than hydroxyapatite under physiological conditions.

Ca/P ratios measured by EDS analysis confirmed the presence of carbonate and $HPO_4^{2-}$ ions measured by FTIR spectroscopy. EDS analysis indicated that the Ca/P ratio decreased with increasing calcium and phosphate ion concentrations in SBF. Specifically, the Ca/P ratios of mineral coatings produced from 2×SBF (1.67±0.03) were higher than mineral coatings produced from 3.5×SBF (1.58±0.05) and 5×SBF (1.43±0.02). Thus, the Ca/P ratio decreased with increasing calcium and phosphate ion concentrations due to a decrease in $CO_3^{2-}$ for $PO_4^{3-}$ and increased incorporation of $HPO_4^{2-}$ at low pH.

Example 3

Effect of Solution Ion Concentrations and pH on Mineral Dissolution

In this Example, the effect of calcium and phosphate ion concentrations and pH of SBF on mineral dissolution was examined.

Specifically, mineral coated films were prepared as described above. Mineral coated films were incubated in DI water with 0.05 M Pipes buffer at pH 7.4 with varying amounts of $CaCl_2$ (0, 0.75, 1.5 or 2.5 mM) and $KH_2PO_4$ (0, 0.3, 0.6 or 1 mM). To determine the influence of pH on mineral dissolution, mineral coated films were incubated in DI water with 0.05 M Pipes buffer with 2.5 mM $CaCl_2$ and 1 mM $KH_2PO_4$ at pH 6.2, 6.6, 7 and 7.4. Mineral coated films in 24-well plates were incubated in 1 ml of each solution at 37° C. for 3 weeks. At specified times, each solution was assayed for soluble calcium and replaced with 1 ml of fresh solution. Mineral dissolution was determined by measuring calcium release into solution. To assay for soluble calcium, a 5 µl aliquot of each solution was added to a 195 µl calcium assay solution having 0.4 mM arsenazo III (MP Biomedicals, Solon, Ohio) in 0.02 M Tris base at pH 7.4. Absorbance at 650 nm was converted to calcium concentration using standard curves relating absorbance intensity to calcium concentration.

Figure 4:
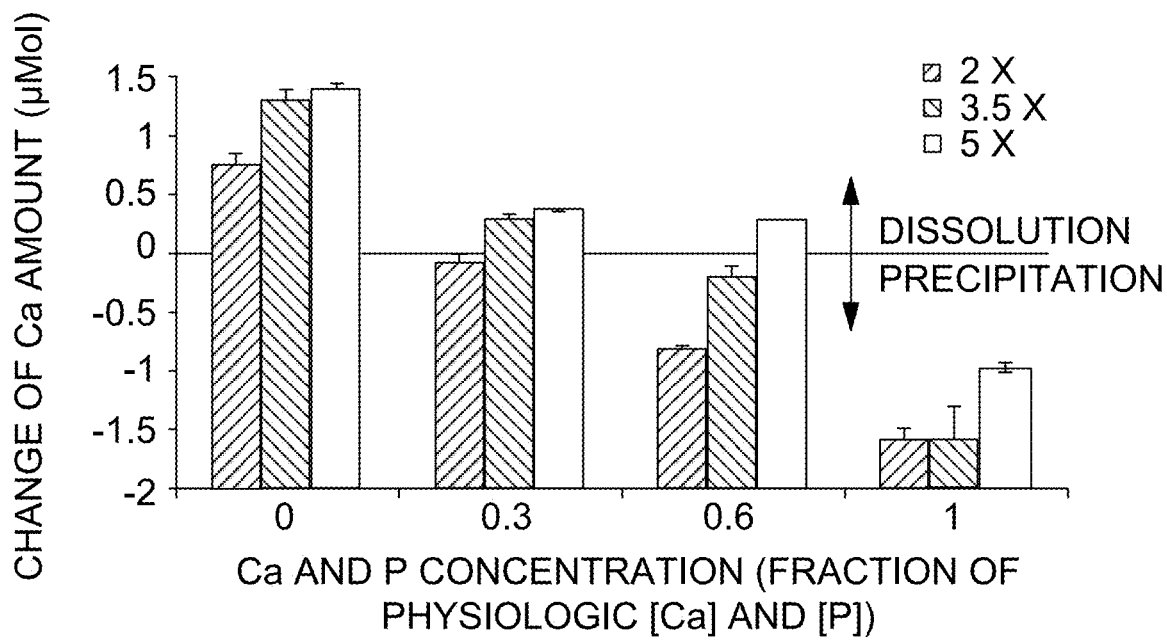
FIG. 4 is a graph showing the change of calcium amount after calcium-phosphate mineral coatings grown on PLG films in 2×SBF, 3.5×SBF and 5×SBF were immersed in solutions containing 0×, 0.3×, 0.6× or 1× physiological calcium and phosphate concentrations at pH 7.4 as discussed in Example 3.
Figure 5:
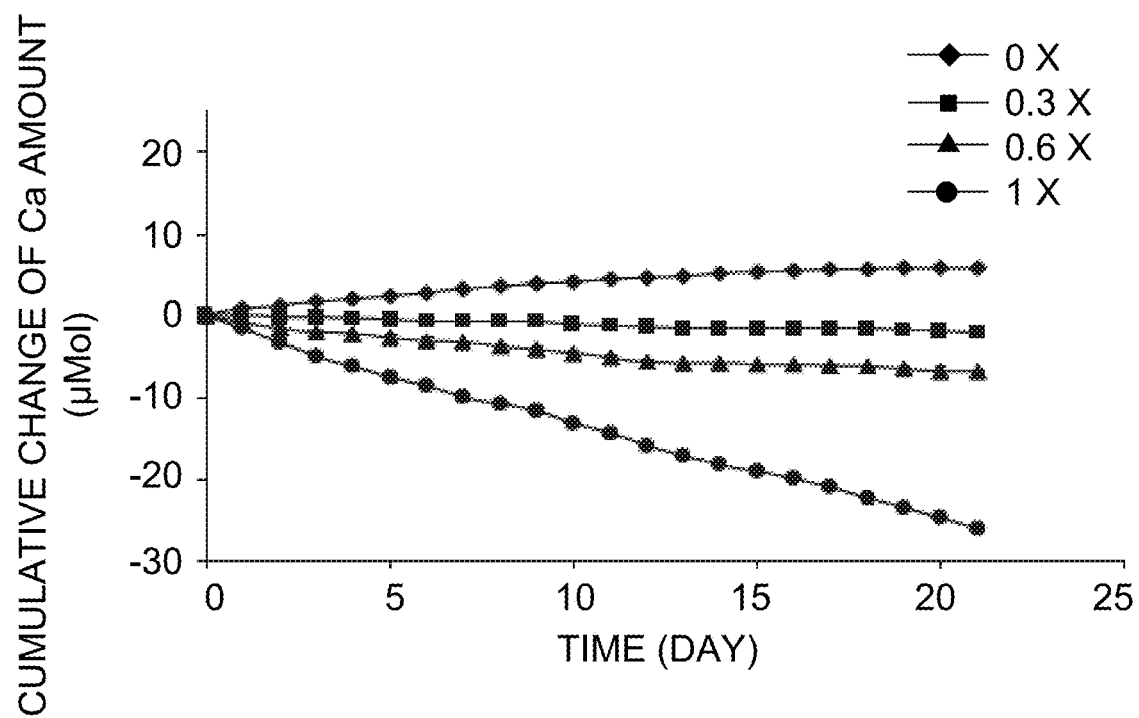
FIG. 5 is a graph showing the cumulative change of calcium amount over time after calcium-phosphate mineral coatings grown on PLG films in 2×SBF, 3.5×SBF and 5×SBF were immersed in solutions containing 0×, 0.3×, 0.6× or 1× physiological calcium and phosphate concentrations at pH 7.4 as discussed in Example 3.

Mineral dissolution increased over time in solutions with decreasing calcium and phosphate ion concentrations at pH 7.4 (see, FIG. 4). The mineral dissolution rate was highest when the mineral coatings were immersed in a solution without calcium and phosphate ions (see, FIG. 5). Mineral dissolution decreased with increasing calcium and phosphate ion concentrations in the dissolution environment, indicating that solution calcium ions were incorporated into the mineral coating during mineral reprecipitation. Calcium ion release from mineral coatings formed in 2×SBF was less than calcium release from mineral coatings formed in 3.5× SBF and 5×SBF in all dissolution environments tested. These results suggested that differences in dissolution rates may correspond to differences in mineral morphology and composition, as well as the increased presence of an OCP phase.

Figure 6:
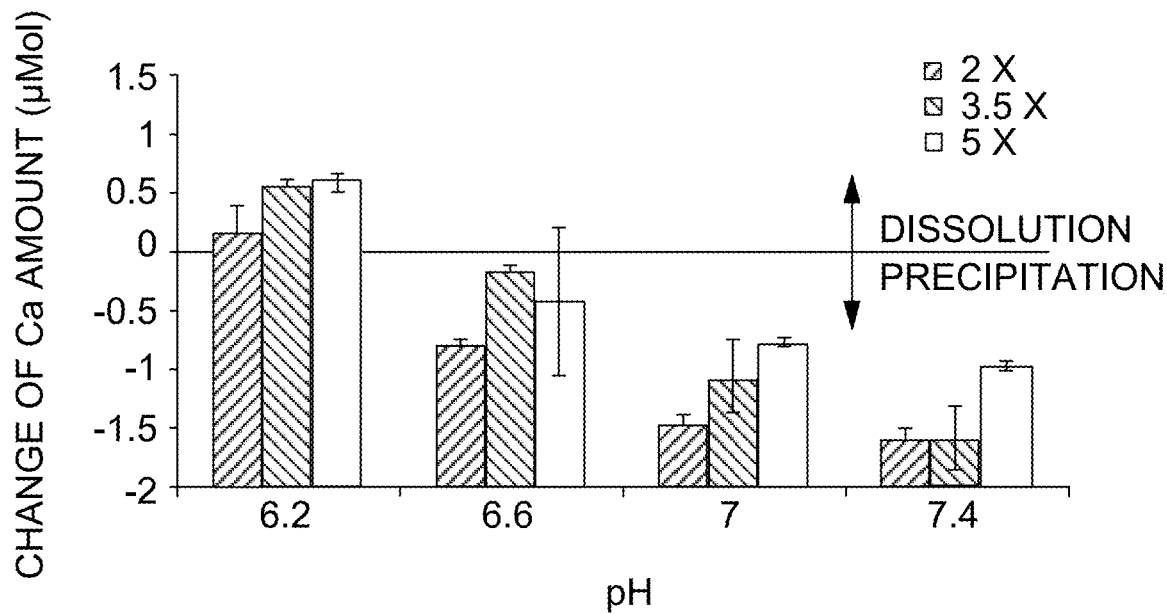
FIG. 6 is a graph showing the change of calcium amount after calcium-phosphate mineral coatings grown on PLG films in 2×SBF, 3.5×SBF and 5×SBF were immersed in solutions containing 1× physiological calcium and phosphate concentrations at varying pH as discussed in Example 3.
Figure 7:
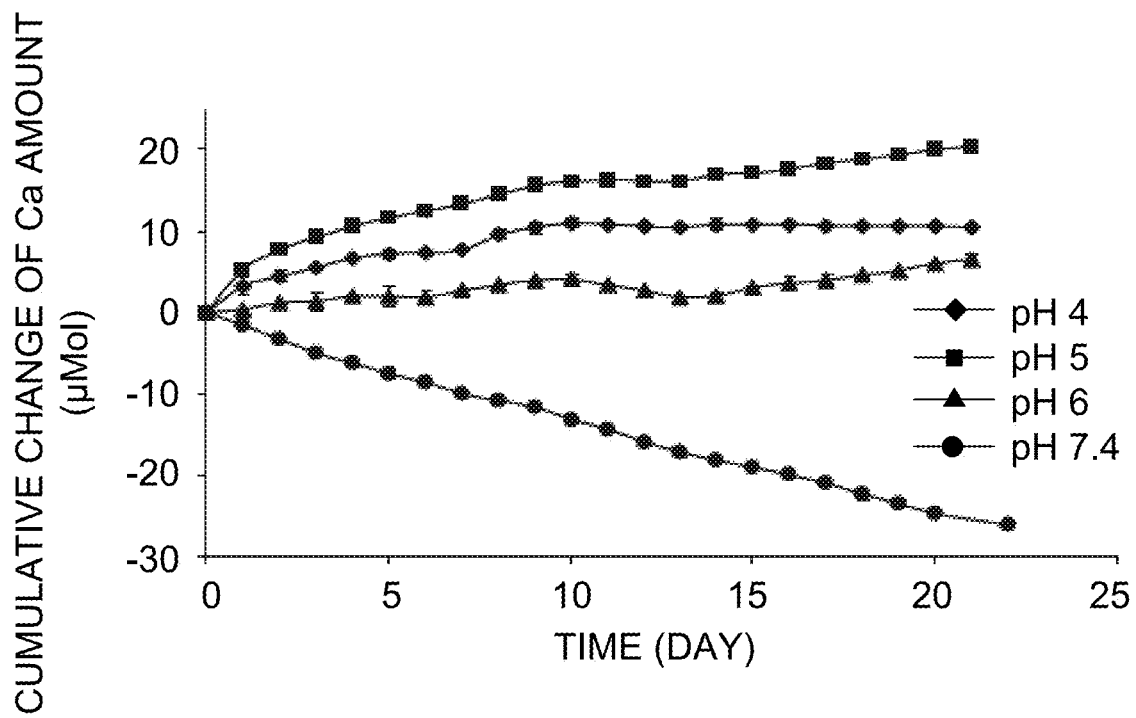
FIG. 7 is a graph showing the cumulative change of calcium amount over time after calcium-phosphate mineral coatings grown on PLG films in 2×SBF, 3.5×SBF and 5×SBF were immersed in solutions containing 1× physiological calcium and phosphate concentrations at varying pH as discussed in Example 3.
Figure 8:
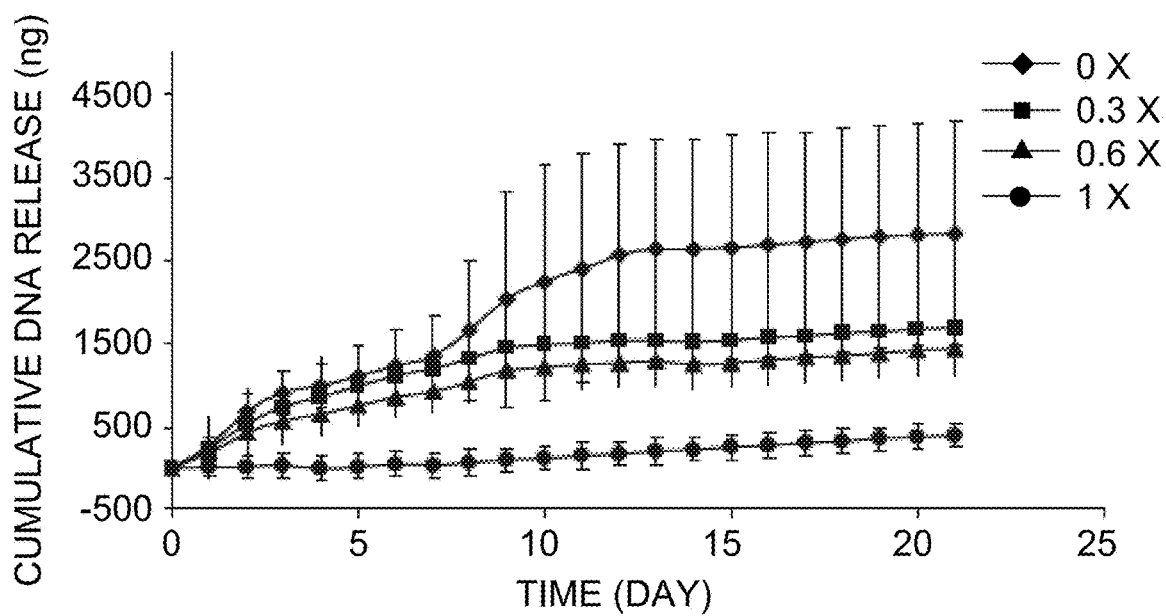
FIG. 8 is a graph showing the cumulative DNA released over time after calcium-phosphate mineral coatings grown on PLG films in 2×SBF, 3.5×SBF and 5×SBF were immersed in solutions containing 0×, 0.3×, 0.6× or 1× physiological calcium and phosphate concentrations at pH 7.4 as discussed in Example 4.

The total calcium release after 24 hours incubation increased linearly with decreasing pH in the dissolution environments (see, FIG. 6). Calcium release from mineral coatings formed in 2×, 3.5× and 5×SBF solutions reached maxima after 24 hours incubation at pH 6.2 (0.150±0.214, 0.546±0.056 and 0.587±0.068 µmol, respectively). The amount of calcium released into the surrounding environment gradually decreased with increasing pH, indicating that calcium was being consumed during mineral reprecipitation at higher pH (see, FIG. 7). The dissolution rate of mineral coatings formed in 2×SBF was lower than the dissolution rates of mineral coatings formed in 3.5×SBF or 5×SBF in the pH range of 6.2-7.4. This result may be attributed to the increased presence of OCP phase in the minerals formed in 3.5×SBF and 5×SBF.

These results demonstrate that the ion concentration and pH of the solution surrounding the mineral coating significantly influenced mineral stability.

Example 4

Plasmid Release from a Mineralized Substrate

In this Example, the release of plasmid DNA ("pDNA") from a mineralized substrate was examined.

Specifically, pDsRed pDNA was amplified in competent TOF10F' *E. coli* (Invitrogen, Carlsbad, Calif.) and purified using a Mega plasmid purification kit (Qiagen, Valencia, Calif.). Mineral coated PLG films were incubated for 1 day in 1 ml of a pDNA buffer containing 20 µg pDNA (10 mM Tris-HCl, 1 mM EDTA, pH 7). Samples were rinsed with DI water and air dried. The amount of bound pDNA was calculated by subtracting the amount of pDNA that remained in the pDNA buffer from the initially added amount of pDNA. The influence of calcium and phosphate ion concentration on pDNA release was characterized by incubating samples in 0.05 Pipes solutions (pH 7.4) containing 0, 0.75, 1.5, or 2.5 M $CaCl_2$ and 0, 0.3, 0.6, or 1 mM $KH_2PO_4$, respectively. The influence of pH on pDNA release was characterized by incubating samples in polynucleotide release media containing 2.5 M $CaCl_2$ and 1 mM $KH_2PO_4$ and buffering these media with either 0.05 M sodium acetate trihydrate (EMD, San Diego, Calif.) (pH 4 or 5) or 0.05 M Pipes (pH 6 or 7.4). Each sample was incubated in 1 ml of polynucleotide release medium in 24-well plates at 37° C. for 3 weeks. At specified times, polynucleotide release medium was removed for analysis and replaced with 1 ml of fresh polynucleotide release medium. A 50 µl aliquot of the polynucleotide release medium was added to 150 µl of a working solution prepared using a Quant-iT Picogreen dsDNA assay kit (Invitrogen, Carlsbad, Calif.). The fluorescence measured at 520 nm was converted to an amount of released pDNA using standard curves prepared with known concentrations of pDNA in solution.

The amount of bound pDNA on the mineral coatings formed in 2×SBF (15.8±1.5 µg) was significantly higher than that on mineral coatings formed in 3.5×SBF (6.1±1.3 µg) or 5×SBF (3.0±0.6 µg). The release rates of pDNA increased with decreasing concentrations of calcium and phosphate ions in the polynucleotide release media, with the largest amount of pDNA released into a polynucleotide release medium devoid of calcium and phosphate ions.

Figure 9:
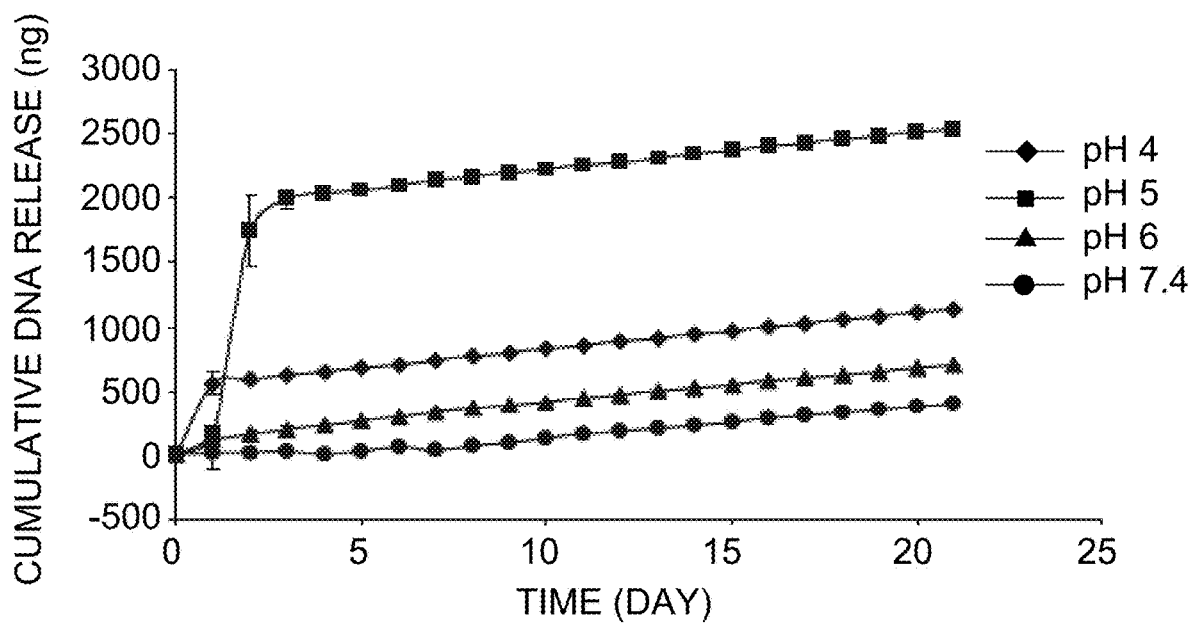
FIG. 9 is a graph showing the cumulative DNA released after calcium-phosphate mineral coatings grown on PLG films in 2×SBF, 3.5×SBF and 5×SBF were immersed in solutions containing 1× physiological calcium and phosphate concentrations at varying pH as discussed in Example 4.

The total amount of pDNA released over time significantly increased as the pH of the polynucleotide release medium decreased. At near physiological pH, the release of pDNA was hindered. As shown in FIG. 9, pH-dependent release of pDNA was directly related to pH-dependent dissolution of mineral coatings. Acidic conditions destabilized the mineral structure more quickly than near neutral media, resulting in greater pDNA release in the low pH condition.

Example 5

Effect of Mineral Coating Morphology on Multipotent Stem Cell Behaviors

In this Example, the effect of mineral coating morphology on multipotent stem cell behaviors was examined.

Specifically, mineral coatings were formed in 2×SBF, 3.5×SBF and 5×SBF solutions containing different calcium and phosphate concentrations and Ca/P ratios as shown in Table 2. As demonstrated in the Examples described above, the morphology of mineral coatings was modulated by changing calcium and phosphate concentrations and Ca/P ratios without creating significant differences in composition, crystallinity and solubility.

Figure 10:
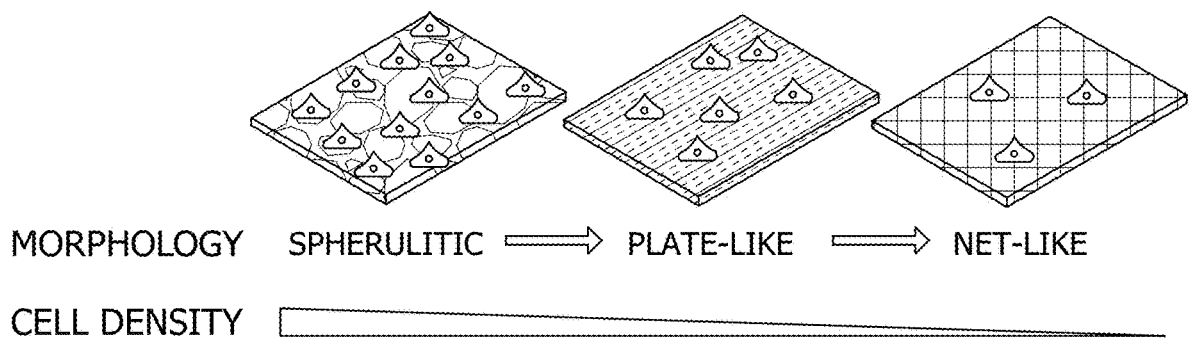
FIG. 10 is a schematic illustration showing the effect of mineral coating morphology on cell density as discussed in Example 5.
Figure 11A:
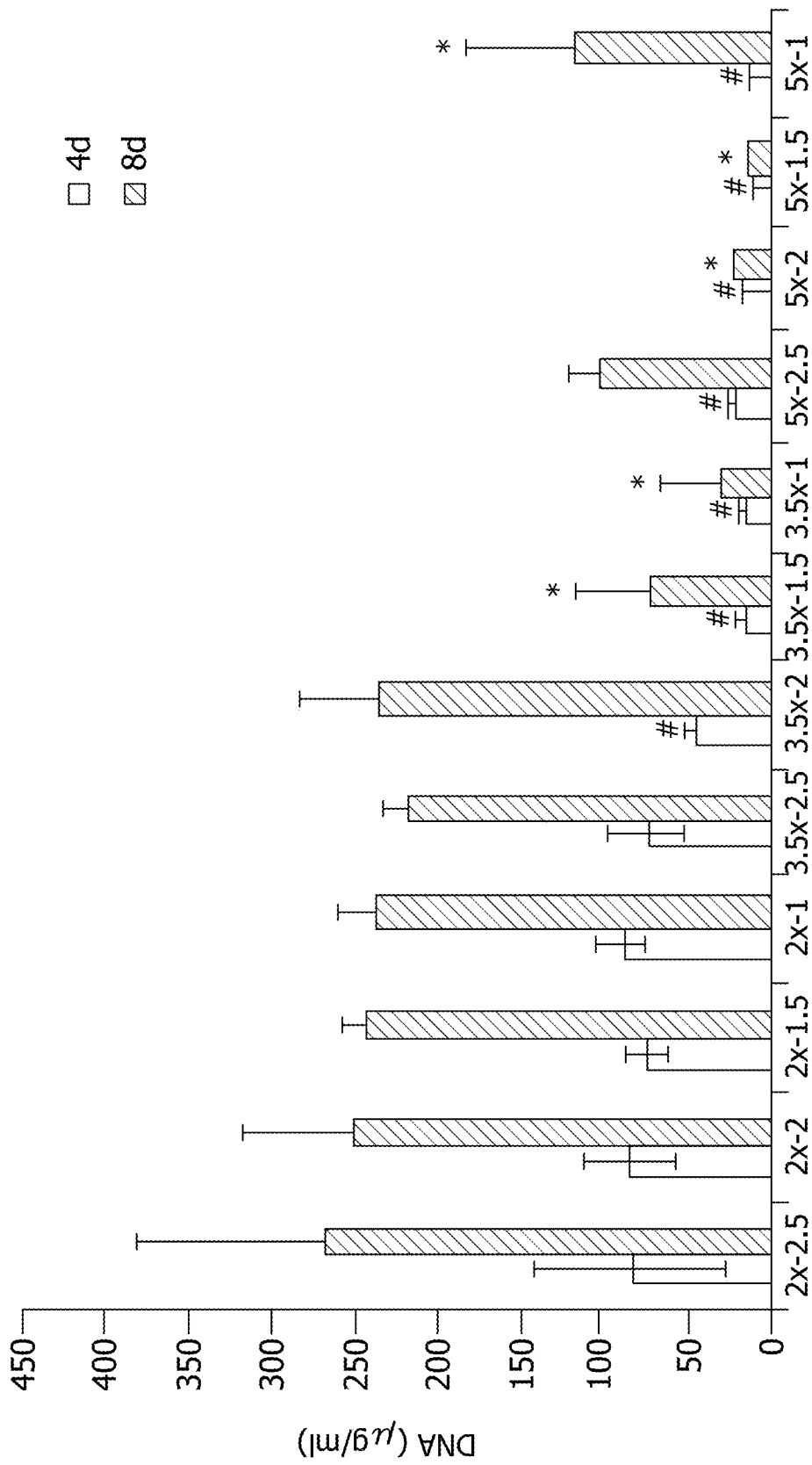
FIG. 11A is a graph showing C3H10T1/2 cell proliferation on mineral coatings as a function of time as discussed in Example 5.
Figure 11B:
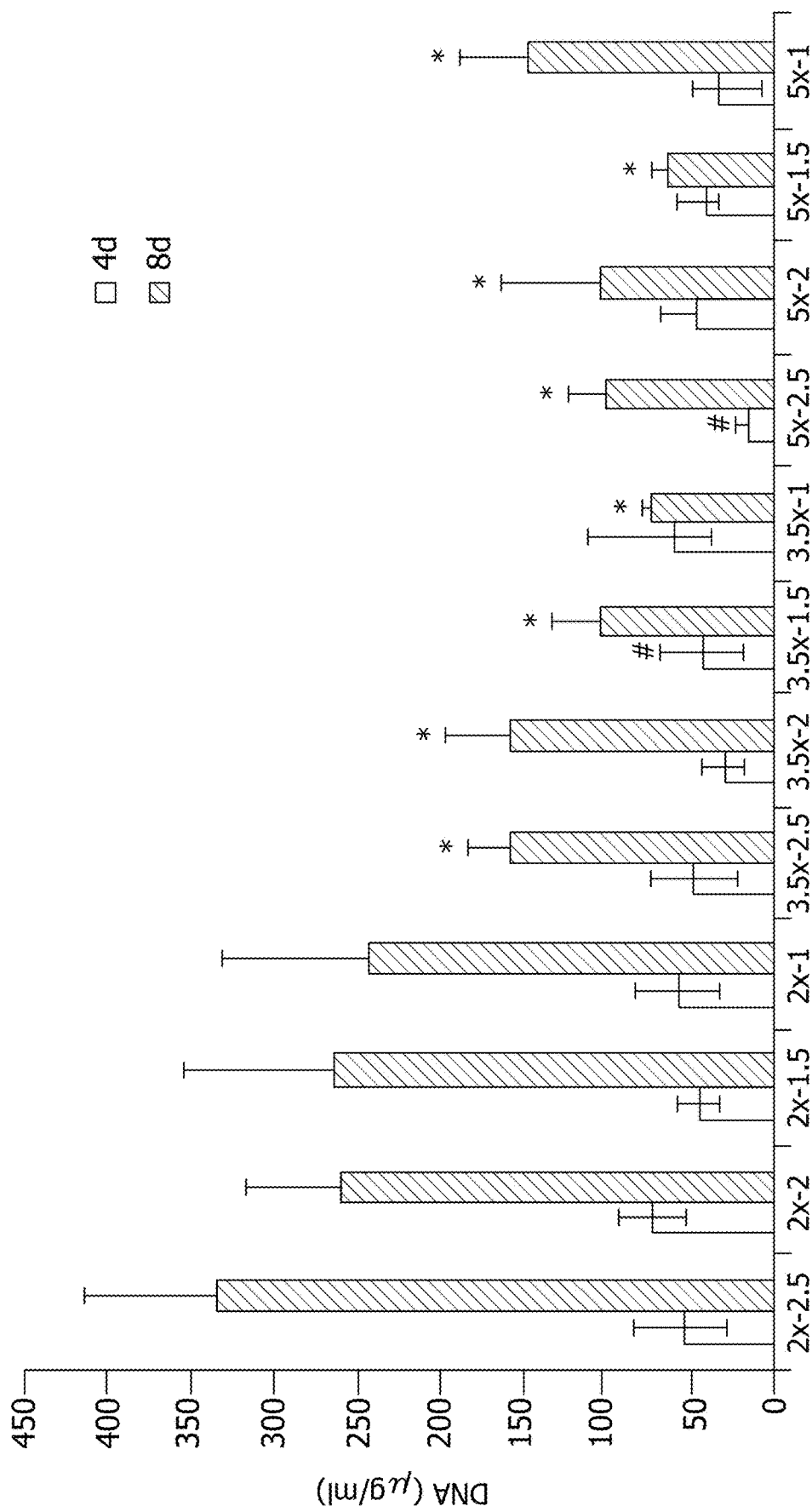
FIG. 11B is a graph showing hMSC proliferation on mineral coatings as a function of time as discussed in Example 5.
Figure 12:
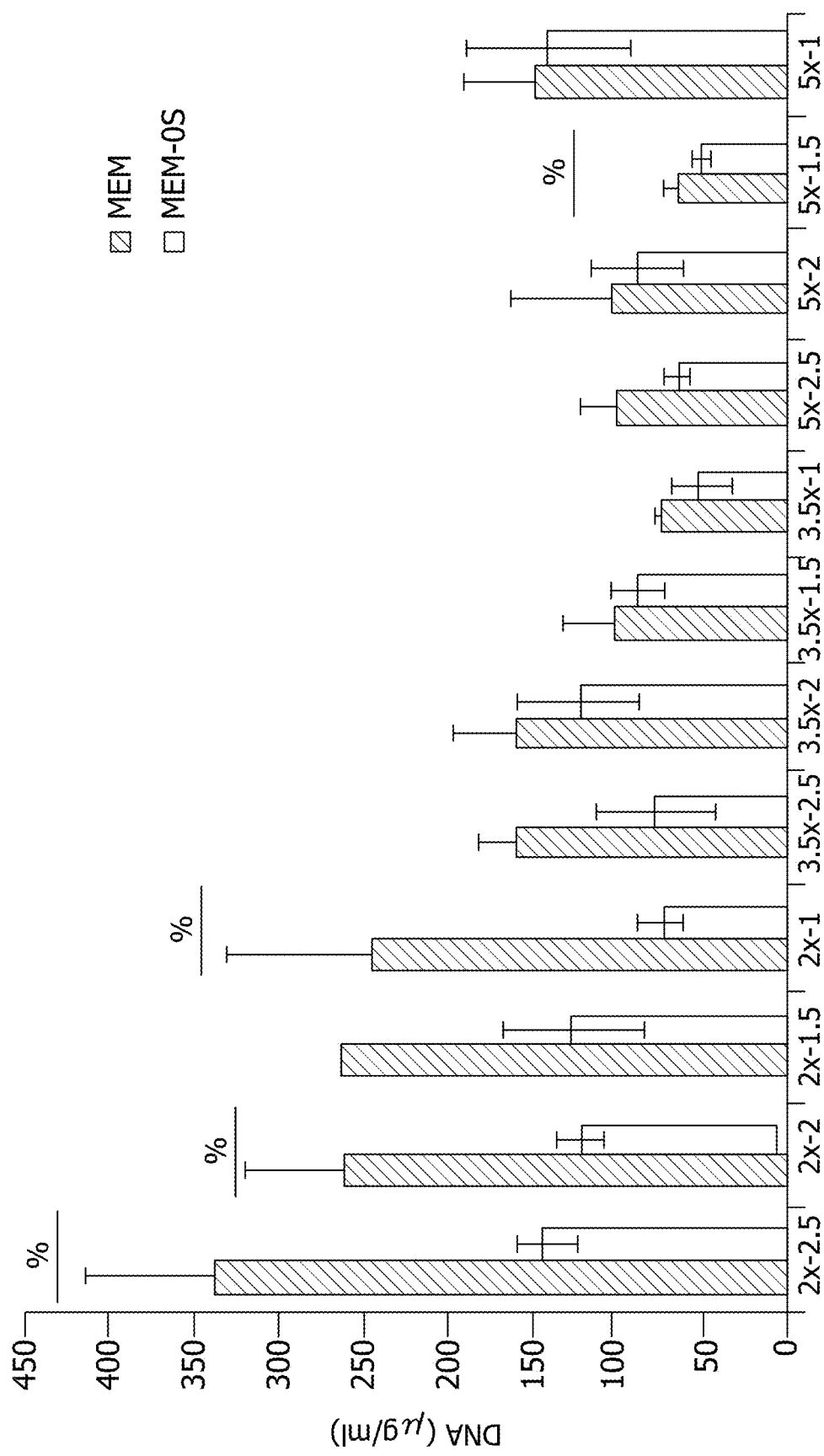
FIG. 12 is a graph showing hMSC proliferation on mineral coatings in MEM and MEM+OS at day 8 as discussed in Example 5.

As illustrated in FIG. 10, the cell density decreased when morphology of mineral coatings was changed from spherulitic microstructure to plate-like or net-like structure. As shown in FIGS. 11A and 11B, cell proliferation on mineral coatings increased with increasing incubation time in cell culture media. Additionally, hMSC proliferation on mineral coatings in MEM+OS was decreased as compared to hMSC proliferation on mineral coatings in MEM.

Example 6

Control of Mineral Coating Dissolution in Cell Culture Conditions

In this Example, the effect of mineral morphology on mineral crystallinity in cell culture conditions was examined.

Specifically, PLG films were mineralized as described above using SBF solutions containing different concentrations of calcium, phosphate, and carbonate and mineral properties were analyzed. Additionally, Ca/P ratio and crystallinity index of mineral coatings with dissolution rate of mineral coatings were compared to determine the change in mineral stability. The dissolution of mineral coatings in cell culture medium (serum-free DMEM) was determined by measuring the change of calcium amount over time.

Figure 13:
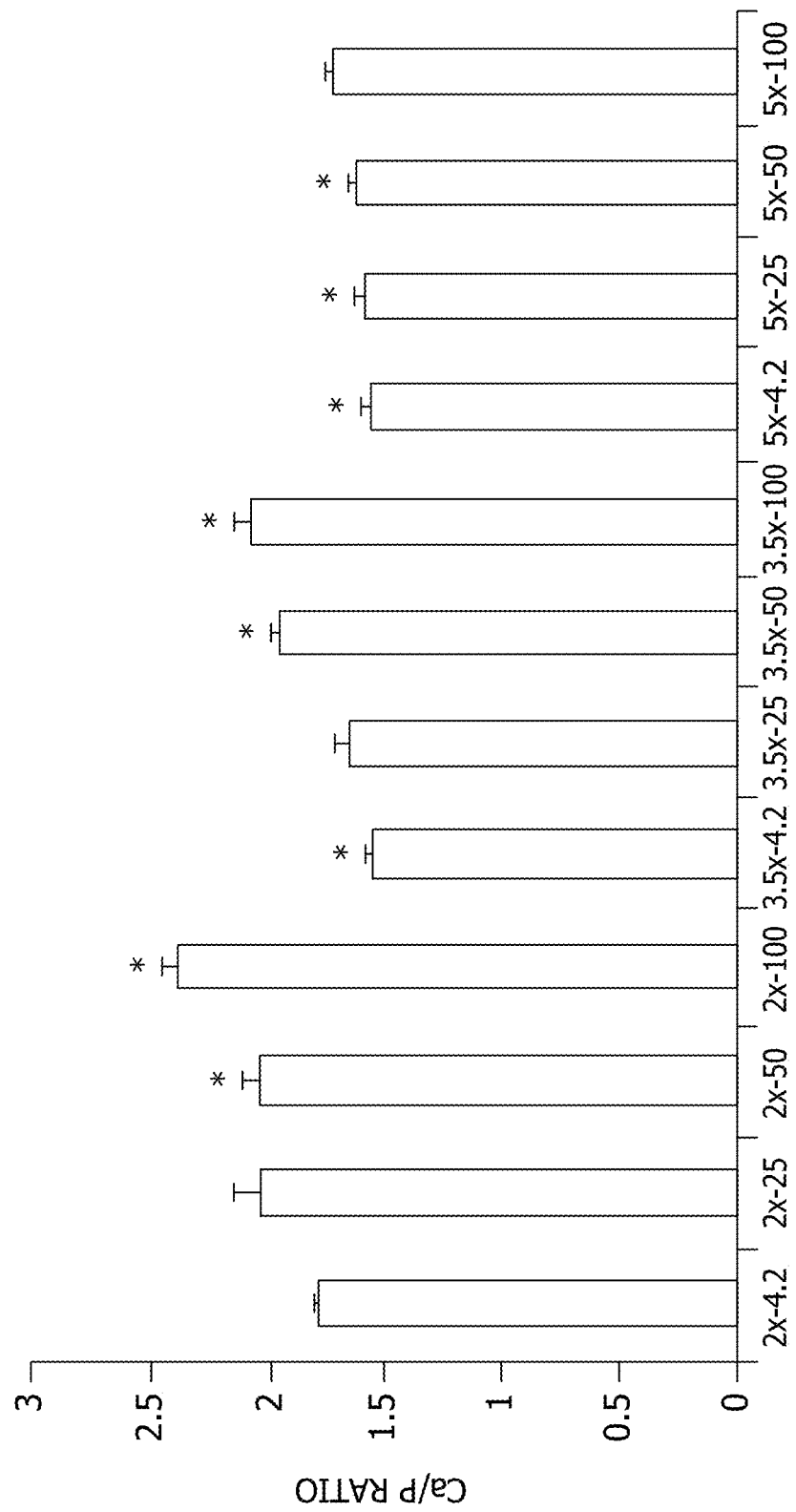
FIG. 13 is a graph showing the calcium/phosphate ratio of mineral coatings grown on PLG films in 2×SBF, 3.5×SBF and 5×SBF having varying carbonate concentrations as discussed in Example 6.
Figure 14:
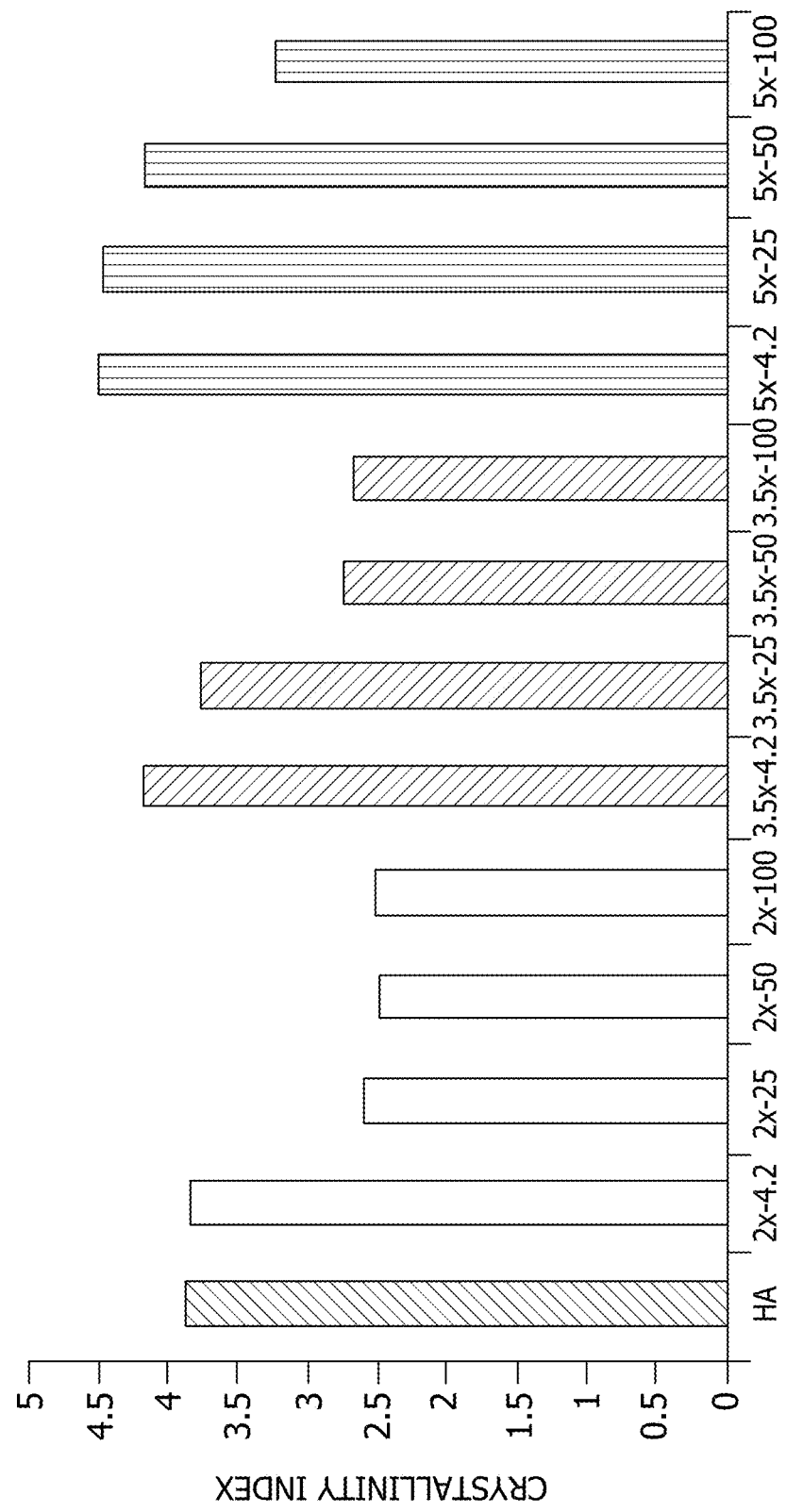
FIG. 14 is a graph showing the crystallinity index of mineral coatings grown on PLG films in 2×SBF, 3.5×SBF and 5×SBF having varying carbonate concentrations compared to hydroxyapatite as discussed in Example 6.
Figure 15:
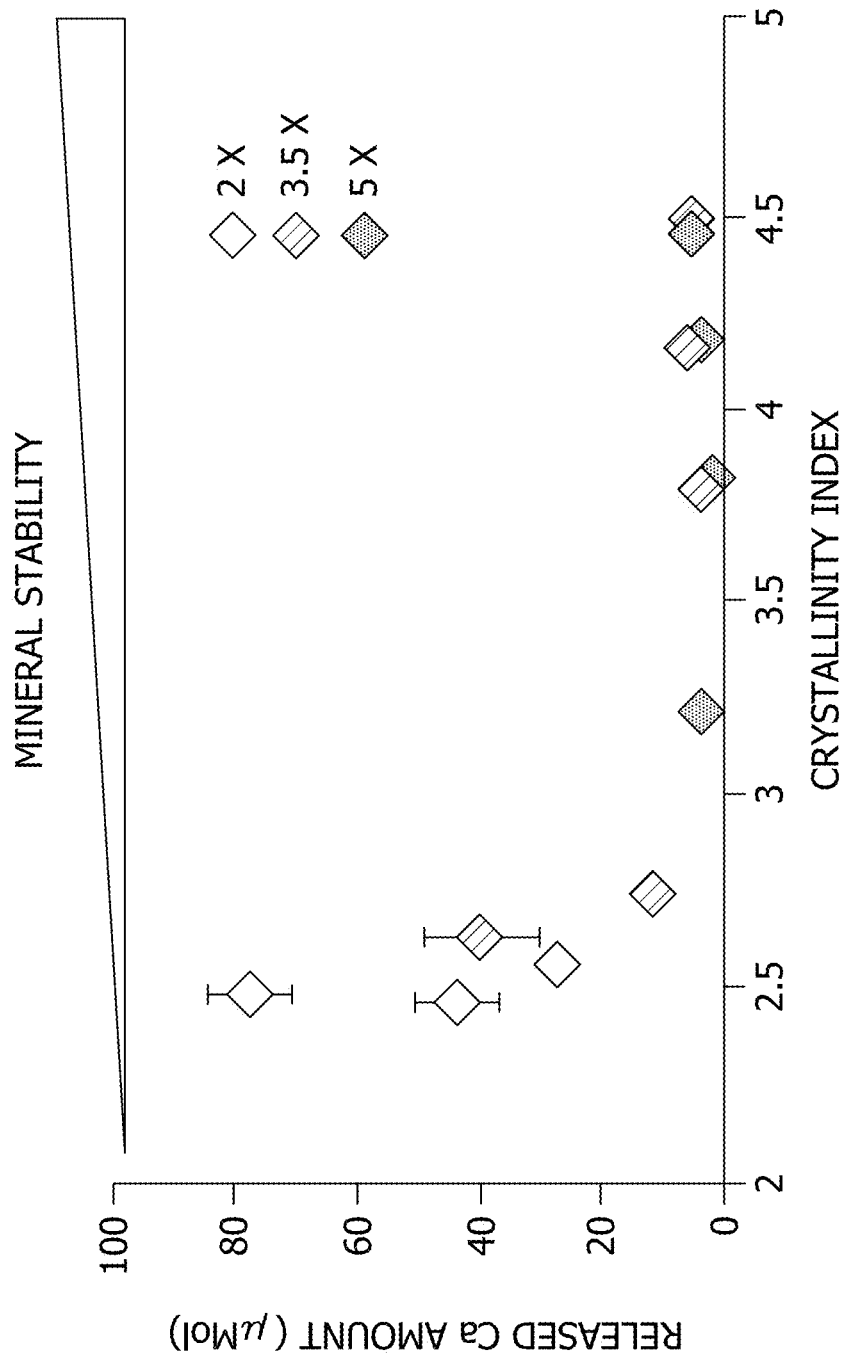
FIG. 15 is a graph showing the crystallinity effect on mineral stability of mineral coatings grown on PLG films in 2×SBF, 3.5×SBF and 5×SBF having varying carbonate concentrations as discussed in Example 6.
Figure 16A:
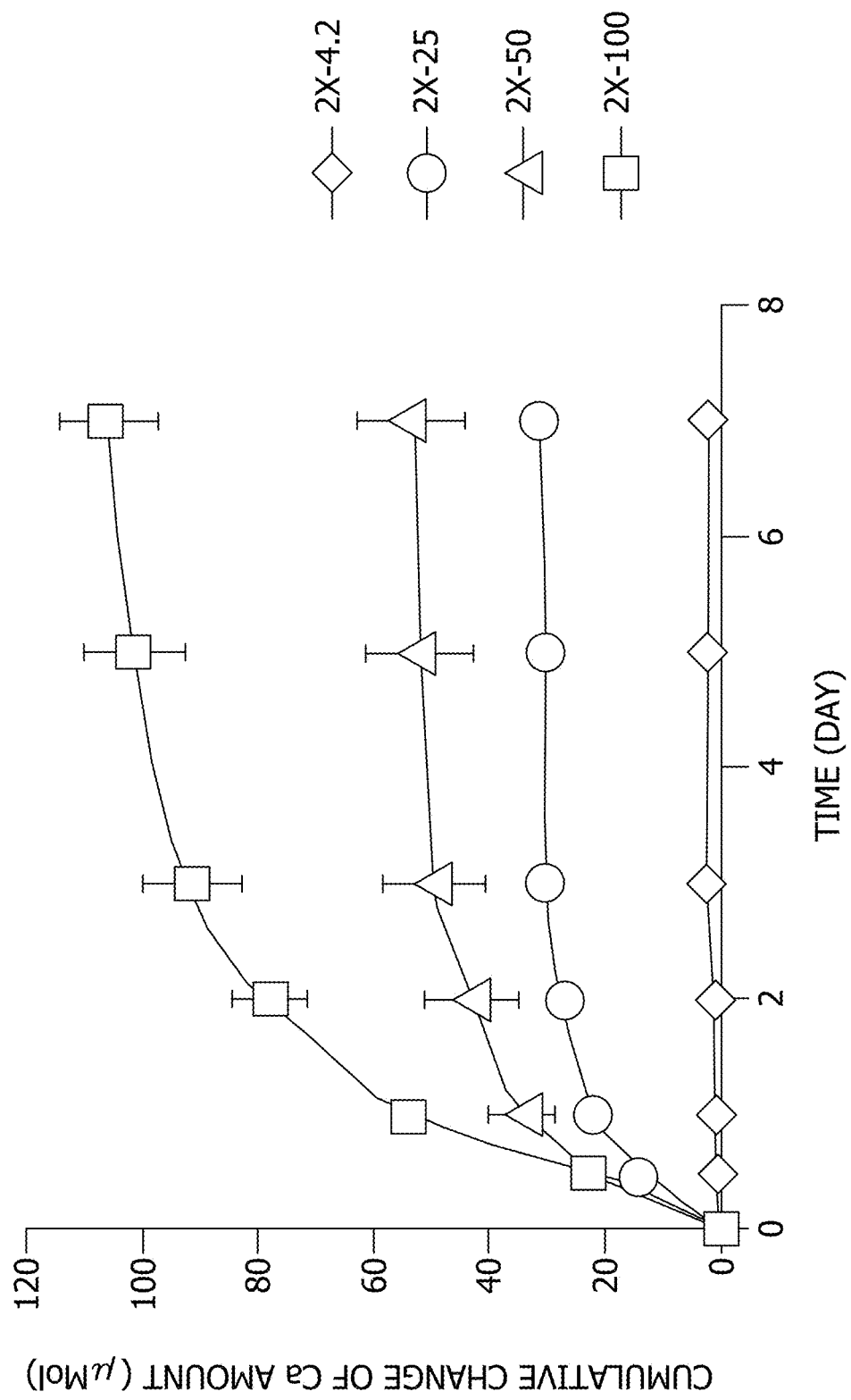
FIGS. 16A-16C are graphs showing the dissolution of mineral coatings in DMEME serum-free medium as discussed in Example 6.
Figure 16B:
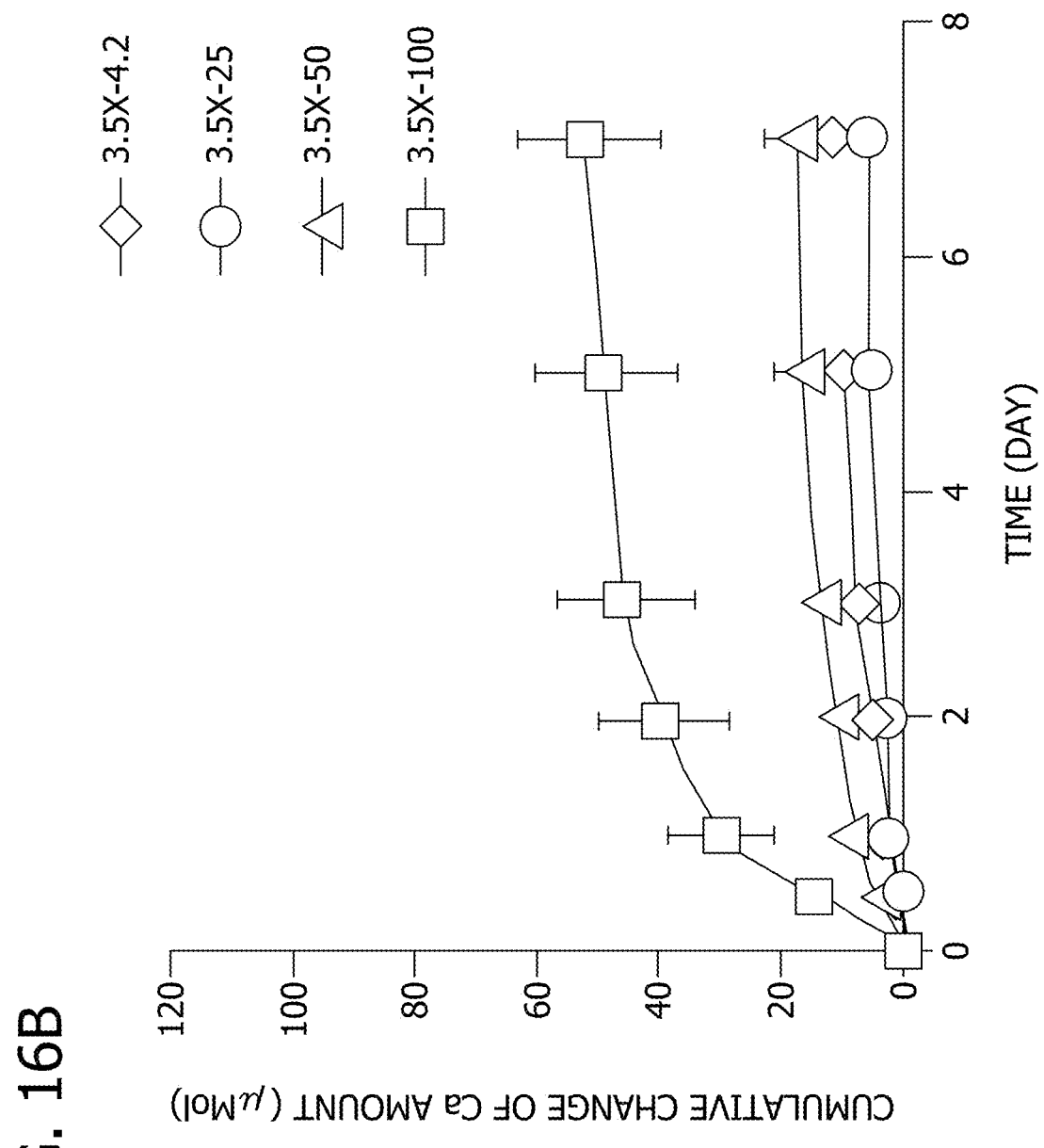
Figure 16C:
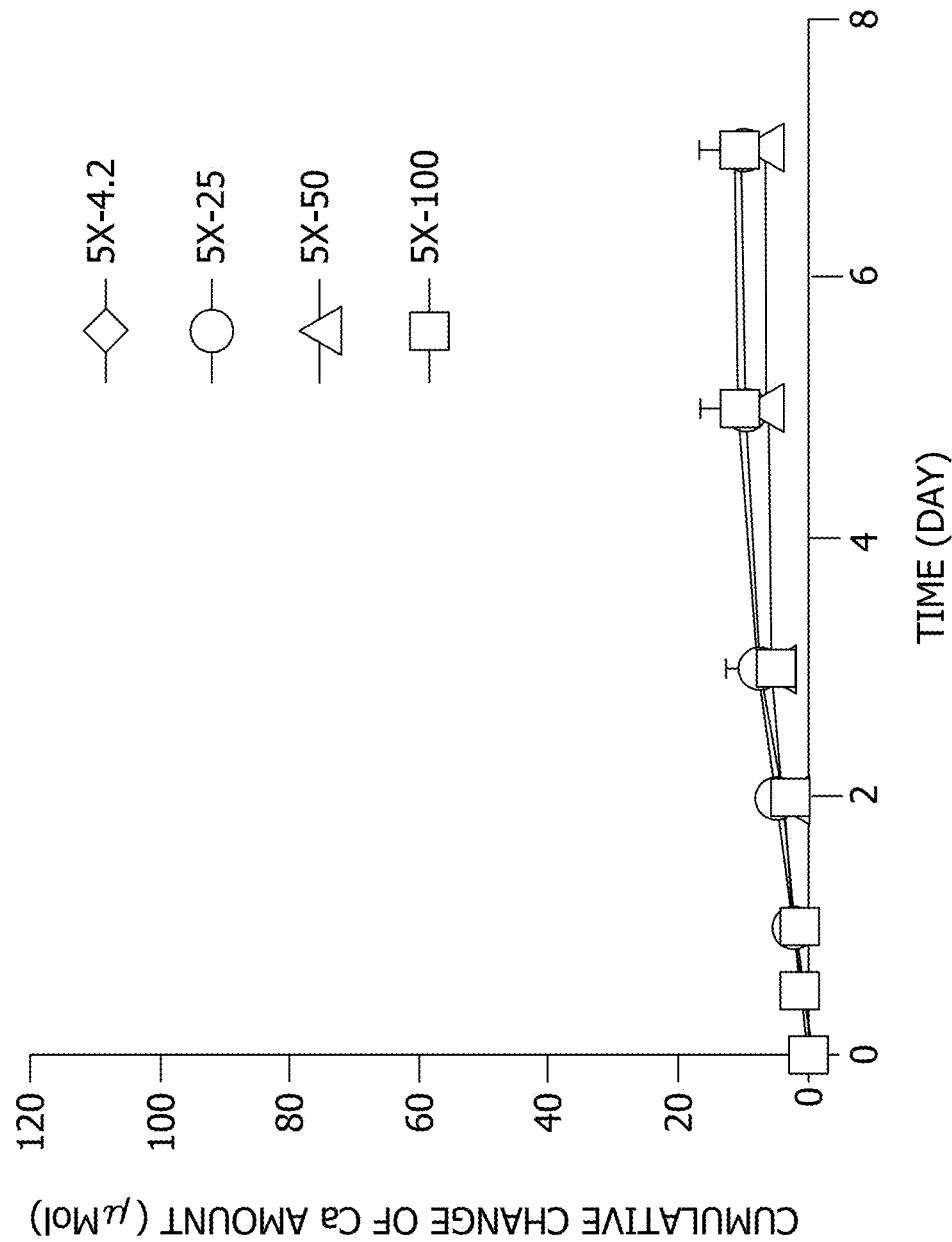

As shown in FIGS. 13 and 14, the calcium/phosphate ratios and crystallinity of mineral coatings grown in 2×SBF, 3.5×SBF, and 5×SBF having varying carbonate concentrations varied. Additionally, as shown in FIG. 15, mineral stability increased with mineral crystallinity FIGS. 16A-16C show that the mineral coating dissolution can occur in DMEM serum-free medium and can be controlled by growing the mineral coatings in specific SBF and varying the carbonate concentrations in the SBF. These results demonstrated that controlling mineral coating morphology with subtle change of mineral crystallinity can allow for controlling mineral dissolution in cell culture conditions.

TABLE 2

Ion concentrations for Ca/P ratio effect on mineral properties (mM).

| $[Ca^{2+}]/[Ca^{2+}]_{in\ blood\ plasma}$ | 2X SBF | | | | 3.5X SBF | | | | 5X SBF | | | |
|---|---|---|---|---|---|---|---|---|---|---|---|---|
| Ca/P | 2.5 | 2 | 1.5 | 1 | 2.5 | 2 | 1.5 | 1 | 2.5 | 2 | 1.5 | 1 |
| $Ca^{2+}$ | 5 | 5 | 5 | 5 | 8.8 | 8.8 | 8.8 | 8.8 | 12.5 | 12.5 | 12.5 | 12.5 |
| $PO_4^{3-}$ | 2 | 2.5 | 3.3 | 5 | 3.5 | 4.4 | 5.8 | 8.8 | 5 | 6.3 | 8.3 | 12.5 |
| $CO_3^{2-}$ | 4.2 | 4.2 | 4.2 | 4.2 | 4.2 | 4.2 | 4.2 | 4.2 | 4.2 | 4.2 | 4.2 | 4.2 |
| pH | 6.8 | 6.6 | 6.5 | 6.2 | 6.1 | 5.8 | 5.8 | 5.7 | 5.8 | 5.7 | 5.5 | 5.3 |

Multipotent stem cells (C3H10T1/2 and human mesenchymal stem cells ("hMSC")) (about 30% of confluence on mineral surface) were seeded with DMEM 10% cosmic calf serum and MEM 10% fetal bovine serum and cultured for 4 days and 8 days. At days 4 and 8, cells were lysed and the supernatant was assayed using a cell proliferation kit (Invitrogen, Carlsbad, Calif.) to measure the total DNA amount. Additionally, hMSC proliferation on mineral coatings during culture in minimum essential medium (MEM) with 10% fetal bovine serum (FBS) and MEM containing 10% FBS with osteogenic supplement (OS) (50 µM ascorbic acid-2-phosphate, 10 mM β-glycerophosphate, and 100 nM dexamethasone) was characterized to determine the effect of OS on hMSC differentiation on mineral coatings.

Example 7

Control of Transfection by Modulating Mineral Stability

In this Example, the effect of mineral stability on transfection of cells cultured on mineral coatings was examined.

Mineral coatings were prepared in 2×SBF, 3.5×SBF and 5×SBF having varying carbonate concentrations as described above. pDNA complexes were immobilized on the mineral coatings by adsorption and co-precipitation methods. pDNA encoding secreted luciferase was used to allow for the continuous measurement of target protein without requiring cell lysis. For transfection, multipotent stem cells (C3H10T1/2 and hMSC) were seeded at a density of 1×10⁴ cell per well with DMEM with 10% cosmic calf serum (C3H10T1/2) and MEM with 10% FBS (hMSC). To determine the transfection rate of cells from dissolving mineral coatings, the luminescence of secreted luciferase after 2 days of cell seeding was screened using an in vivo image system. At specific time points, cell culture medium containing secreted luciferase was collected and assayed with Cell-Glow luciferase kit (Clontech, Mountain View, Calif.). To measure luciferase activity, luminescence was measured using a microplate luminometer (Veritas, Sunnyvale, Calif.). Transfection of C3H10T1/2 and hMSC was measured by dividing luciferase activity by cell viability, which was measured using CellTiter-Blue cell viability assay kit (Promega, Madison, Wis.).

Figure 17:
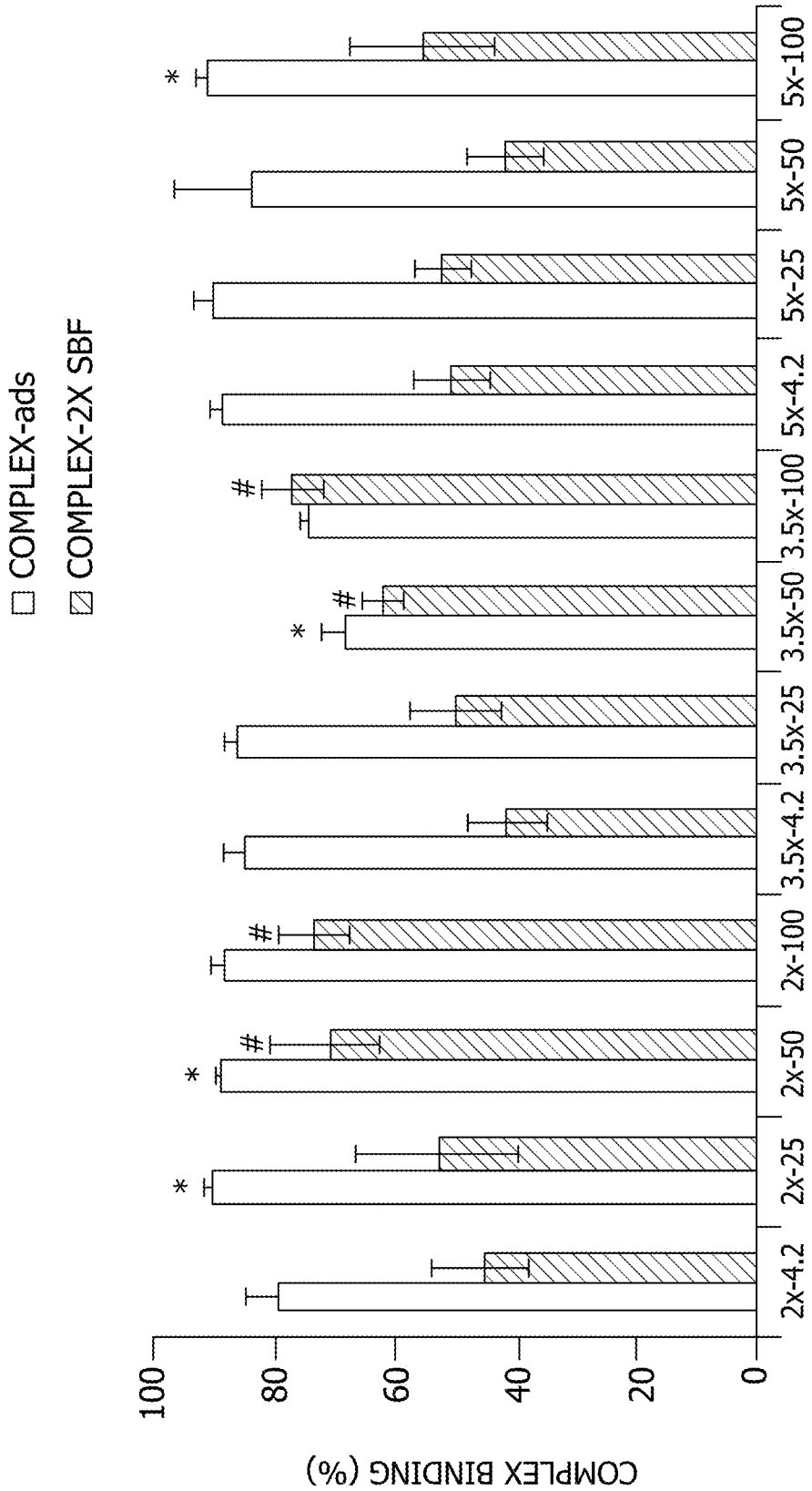
FIG. 17 is a graph showing pDNA complex binding efficiency after adsorption and co-precipitation on mineral coatings grown on PLG films in 2×SBF, 3.5×SBF and 5×SBF having varying carbonate concentrations as discussed in Example 7.
Figure 18A:
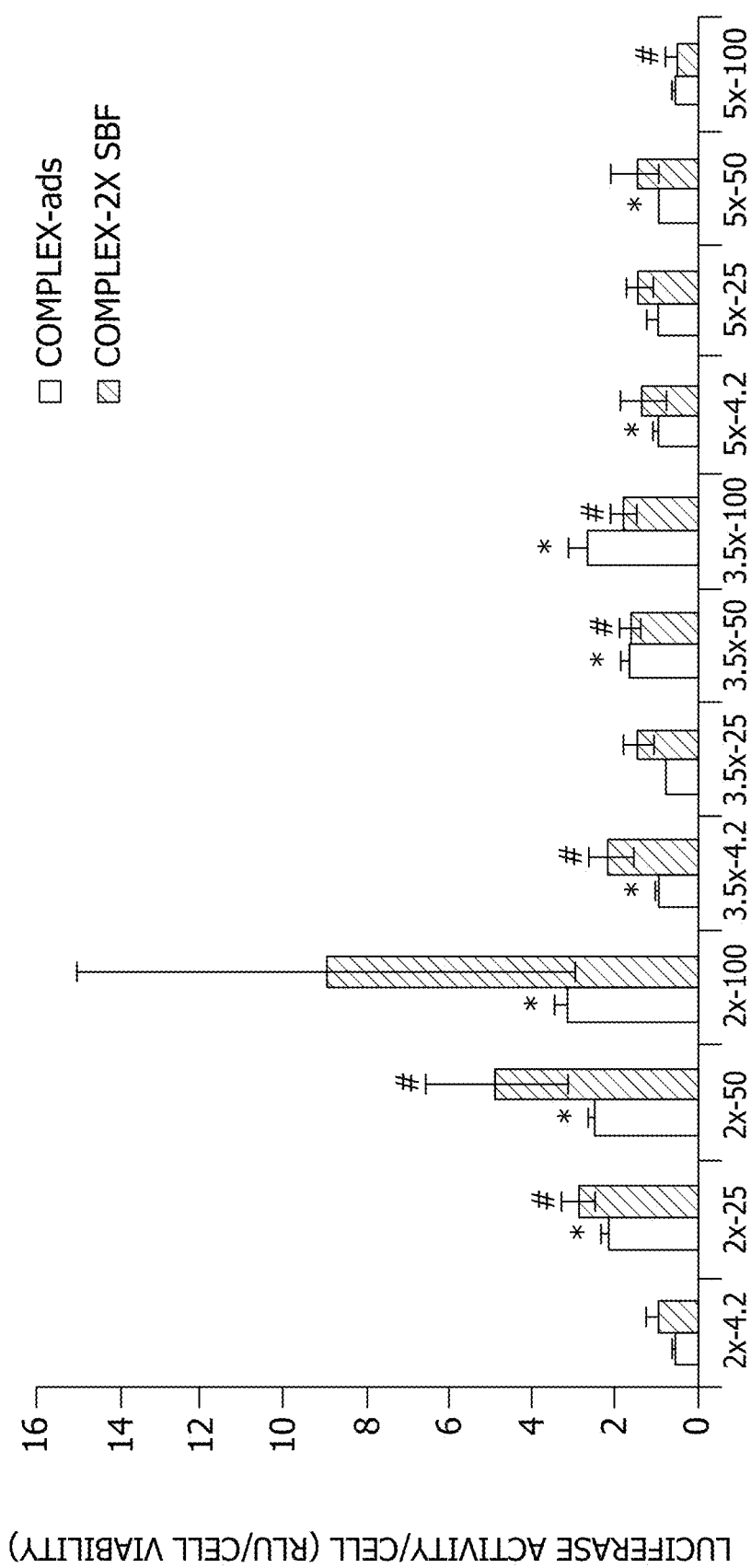
FIG. 18A is a graph showing the luciferase activity of C3H10T1/2 cells cultured on mineral coatings grown on PLG films in 2×SBF, 3.5×SBF and 5×SBF having varying carbonate concentrations as discussed in Example 7.
Figure 18B:
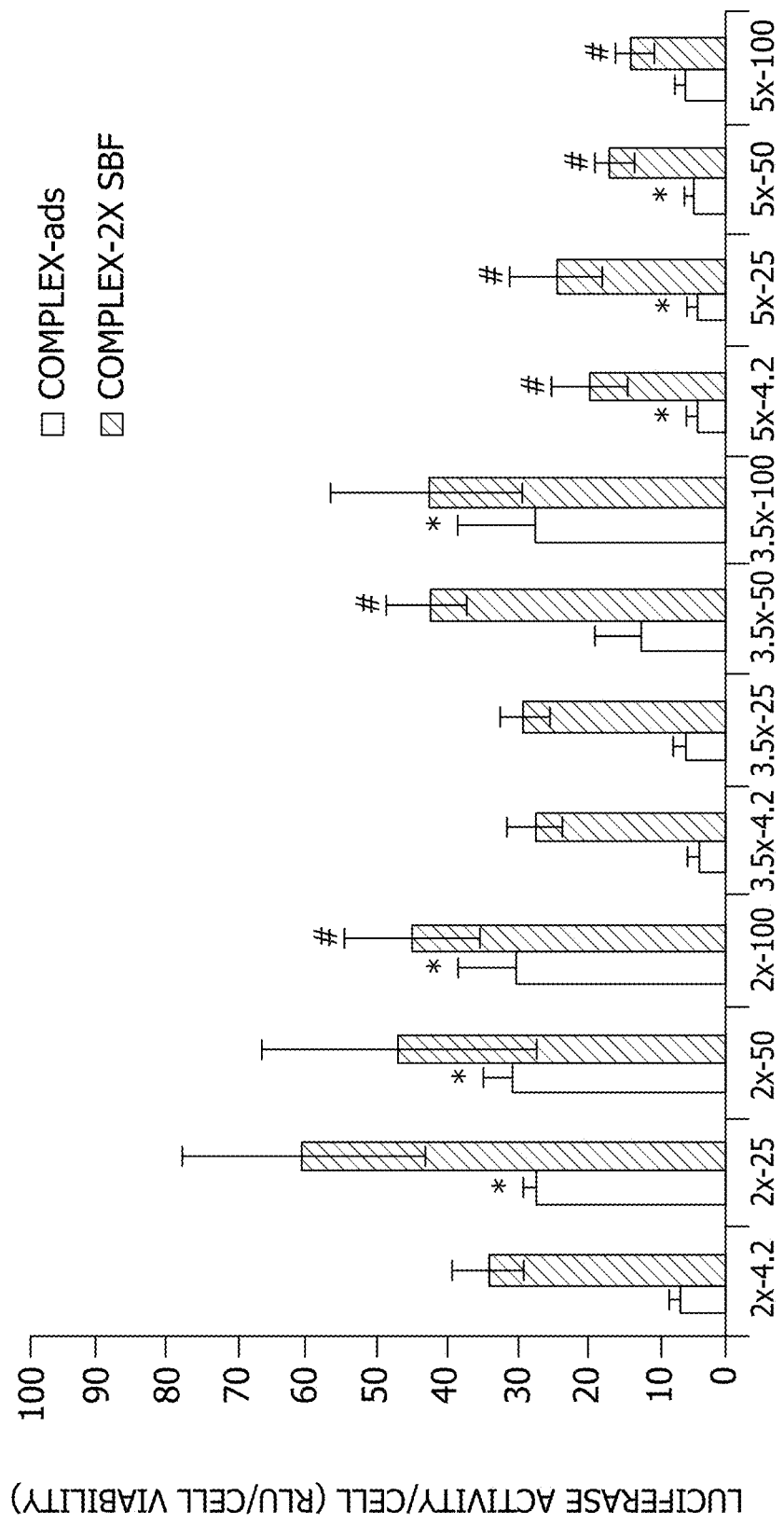
FIG. 18B is a graph showing the luciferase activity of hMSC cultured on mineral coatings grown on PLG films in 2×SBF, 3.5×SBF and 5×SBF having varying carbonate concentrations as discussed in Example 7.

As shown in FIG. 17, pDNA complex binding was dependent on the binding method. As shown in FIGS. 18A and 18B, luciferase activity of C2H10T1/2 (FIG. 18A) and hMSC (FIG. 18B) after 2 days culture on mineral coatings indicated a significant difference compared to 2×-4.2 condition by adsorption and co-precipitation. The transfection of cells on mineral coatings containing adsorbed pDNA complexes was correlated with the mineral stability change. These experiments demonstrated that non-viral transfection of cells can be controlled by changing mineral properties. These results also demonstrated that the relative luminescent intensity can be screened in an enhanced high throughput format using an in vivo image system. These results further demonstrated that many different mineral coatings can be prepared that can then be used as a platform for high throughput transfection of cells for screening.

Example 8

Transfection of Human Umbilical Vein Endothelial Cells on Mineral Coatings

In this Example, transfection of human umbilical vein endothelial ("HUVEC") cells cultured on mineral coatings was examined.

Specifically, HUVEC were cultured on mineral coatings in M199 medium with 20% FBS and EGM-2 after immobilization of pDNA complexes encoding secreted luciferase on mineral coatings by adsorption and co-precipitation methods. At specific time points, cell culture media containing secreted luciferase were collected for luciferase assay as described above. Cell viability was measured using a microplate reader (Bio Tek, Winooski, Vt.). The results are shown FIG. 19.

Figure 19:
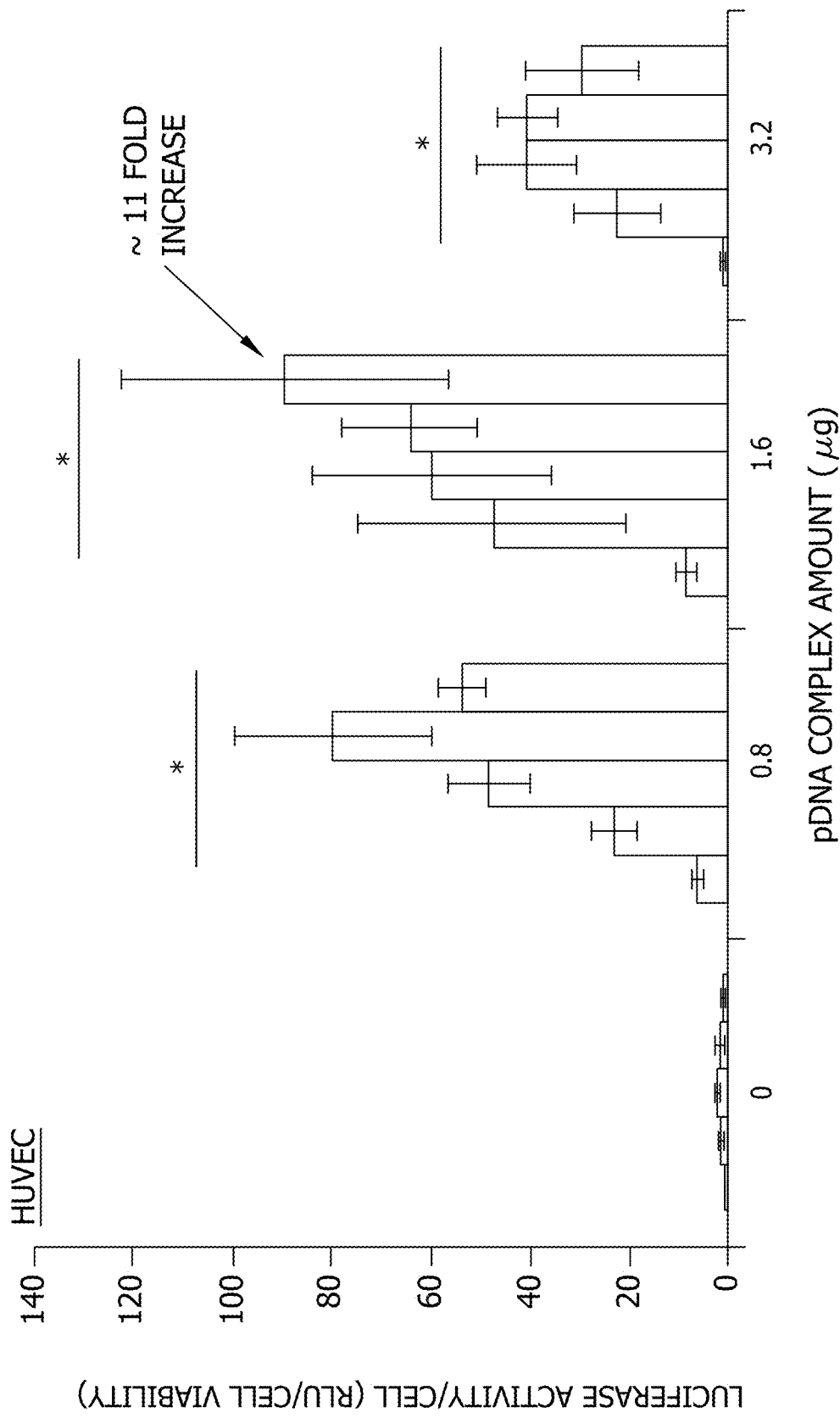
FIG. 19 is a graph showing the luciferase activity of HUVECs cultured on mineral coatings grown on PLB films having varying mineral properties and pDNA complex amounts as discussed in Example 8.

As shown in FIG. 19, combinatorial changes in mineral properties and pDNA complex amount identified conditions in which the luciferase activity per cell was increased by 11-fold for primary HUVECs. This fold increase is relative to standard manufacturer protocols using pDNA-Lipofectamine complexes in solution. In addition to the high levels of transfection relative to standard commercial techniques, combinatorial variation in mineral properties and pDNA complex amounts also resulted in controllable levels of transfection, and collectively the data show conditions in which the luciferase activity can be varied over a broad range of values.

Example 9

In this Example, non-viral human mesencymal stem cell (hMSC)-transfection using mineral coated 3D scaffold array was examined.

PLG scaffolds were fabricated in a poly(propylene) 96-well plate using PLG (10% w/v) in acetone with a salt fusion/solvent casting/salt leaching technique. NaCl particles were previously sieved to 250-425 μm and used as porogen. 130 mg NaCl was placed in each well of the 96-well plate and incubated in a 95% humidity cell culture incubator at 37° C. for 4 h for salt fusion. Then the fused salt template was dried overnight in an oven at 50° C. 30 μL of the PLG solution was added into each well and the whole plate was centrifuged at 2000 RPM to wet all the NaCl particles. After evaporating the solvent, the whole plate was then immersed in a 4.0 L beaker filled with DI water to leach out the salt particles. The water was refreshed every 4 h and the leaching process took approximately 48 h.

To coat the PLG scaffolds with mineral, the scaffold was treated with 200 μL 0.1 M NaOH for 5 min at room temperature to activate the COOH and OH groups on the polymer surface. 200 μL of various SBF solutions (Table 3) was then added into each well of scaffolds after extensively washing out the NaOH residue. The SBF solution was renewed every 12 h to maintain a consistent ionic strength for 7 days. The morphology of the PLG scaffold before and after mineral coatings was observed using scanning electron microscopy. Mineral coated PLG scaffold was stained using Alizarin Red S (Sigma-Aldrich, St. Louis, Mo.) for identifying calcium on the scaffold.

TABLE 3

Ion concentrations for $CO_3^{2-}$ effect on mineral properties (unit: mM)

| $[Ca^{2+}]$ & $[PO_4^{3-}]$ in blood plasma | | | | | 2X | | | | 3.5X | | | | 5X | | | |
|---|---|---|---|---|---|---|---|---|---|---|---|---|---|---|---|---|
| $Ca^{2+}$ | 5 | 5 | 5 | 5 | 8.8 | 8.8 | 8.8 | 8.8 | 12.5 | 12.5 | 12.5 | 12.5 |
| $PO_4^{3-}$ | 2 | 2 | 2 | 2 | 3.5 | 3.5 | 3.5 | 3.5 | 5 | 5 | 5 | 5 |
| $CO_3^{2-}$ | 4.2 | 25 | 50 | 100 | 4.2 | 25 | 50 | 100 | 4.2 | 25 | 50 | 100 |
| pH | 6.8 | 6.8 | 6.8 | 6.8 | 6.1 | 6.1 | 6.1 | 6.1 | 5.8 | 5.8 | 5.8 | 5.8 |

Figure 20A:
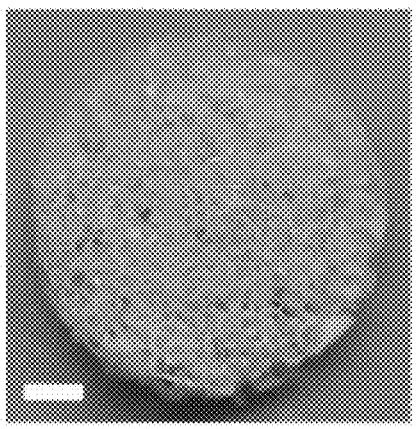
FIGS. 20A-20D are photographic images (A, B) and SEM images (C, D) showing mineral coating formation on 3-dimensional PLG scaffolds before mineralization (A, C) and after mineralization (B, D) as discussed in Example 9. Scale bars, 1 mm for photograph images and 100 μm for SEM images.
Figure 20B:
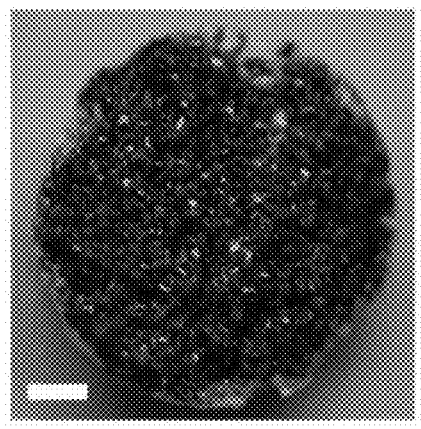
Figure 20C:
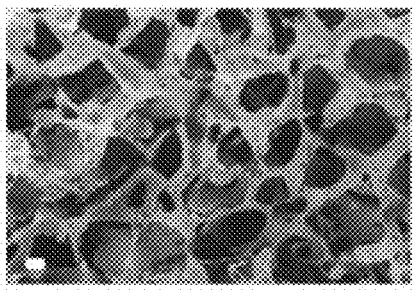
Figure 20D:
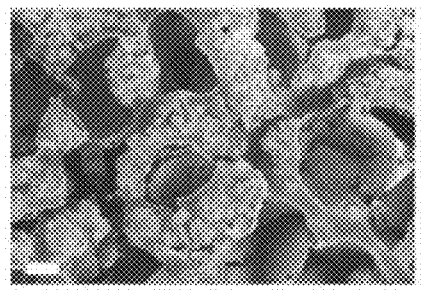

The gross view of the 3D PLG scaffold is shown in FIG. 20A. Highly porous scaffold was generated using the current approach. The morphology of the 3D scaffold was also examined by scanning electron microscopy and shown in FIG. 20C. The pore size of the scaffold was approximately between 250-400 μm. The mineral coating formed on the scaffold was illustrated by Alizarin Red S staining which showed uniform mineral coating formed through the whole scaffold (FIG. 20B). The morphology of the coating was also visualized by electron microscopy which also showed the coverage of the mineral over the scaffold structure while retaining the original porous structure (FIG. 20D).

The procedure for the transfection was similar to that of mineral coatings on PLG surfaces with some adjustments: 1 μg plasmid DNA was used for each scaffold; plasmid DNA binding was conducted in 100 μL pDNA/Lipofectamine 2000 complex containing medium; hMSC was seeded on the mineral coated scaffolds with complexes at a density of $1.0 \times 10^5$ cells/scaffold. After 2 d of cell culture on mineral scaffolds, each medium was taken for luciferase activity assay and total protein amount on each scaffold was measured by micro BCA kit (Thermo Scientific, Rockford, Ill.).

Figure 21:
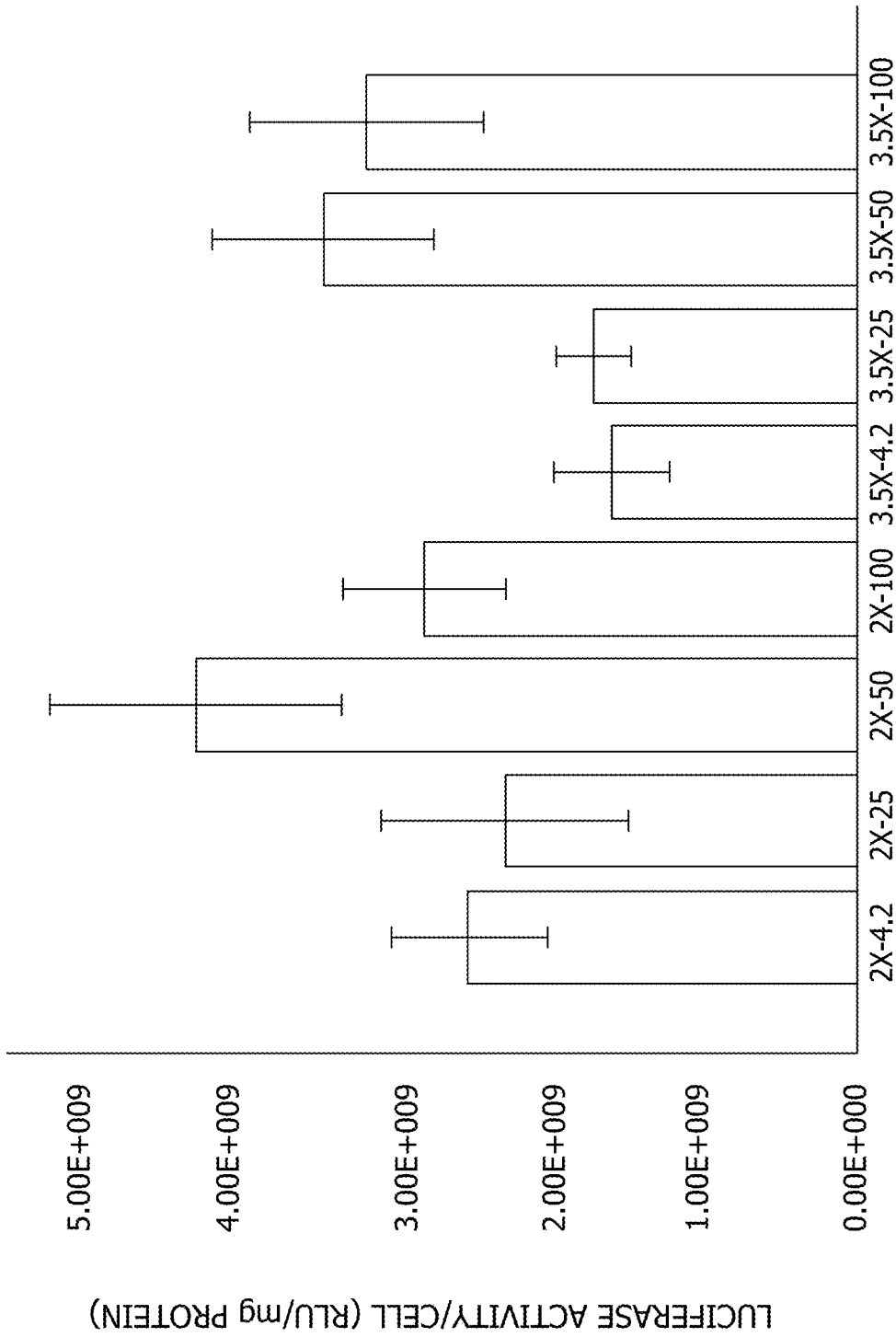
FIG. 21 is a graph showing luciferase activity of hMSCs after 2 days culture on mineralized 3-dimensional PLG scaffolds containing pDNA complexes as discussed in Example 9. Data represents mean±SD (n=4).

This Example exhibits that cell transfection could also be achieved by mineral coating in a 3D scaffold format. The luciferase activity of coating with high carbonate content generally showed higher cell transfection efficiency. The peak value of transfection was observed when 2×-50 SBF was used to form the mineral coating (FIG. 21).

The examples described above demonstrate that the mineral coatings and transfection methods offer the ability to non-virally transfect cells. Surprisingly, use of the mineral coatings of the present disclosure for transfection showed 150-fold greater transfection rates when compared to other commercially-available transfection methods. The mineral coatings and transfection methods of the present disclosure further allow for a high throughput systematic screen for controlling and enhancing the transfection of cells.

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A non-viral transfection system comprising:
   a substrate that comprises:
      a mineral coating, wherein the mineral coating comprises a calcium to phosphate ratio of from about 2.5:1 to about 1:1;
      a polynucleotide-lipid complex bound to the mineral coating; and
      one or more cells.

2. The non-viral transfection system of claim 1, wherein the substrate further comprises a poly($\alpha$-hydroxy ester).

3. The non-viral transfection system of claim 2, wherein the poly($\alpha$-hydroxy ester) is selected from the group consisting of poly(L-lactide), poly(lactide-co-glycolide), poly($\epsilon$-caprolactone), and combinations thereof.

4. The non-viral transfection system of claim 1, wherein the substrate is selected from the group consisting of a film, a plate, a dish, a coverslip, and a slide.

5. The non-viral transfection system of claim 1, wherein the mineral coating comprises a morphology selected from the group consisting of a spherulitic microstructure, a plate-like microstructure, a net-like microstructure, and combinations thereof.

6. The non-viral transfection system of claim 5, wherein the spherulitic microstructure comprises an average spherulite diameter of from about 2 µm to about 4 µm.

7. The non-viral transfection system of claim 1, wherein the substrate comprises more than one well or more than one chamber.

8. The non-viral transfection system of claim 1, wherein the cell is selected from the group consisting of a pluripotent stem cell, a mesenchymal stem cell, and an umbilical vein endothelial cell.

9. The non-viral transfection system of claim 1, wherein the substrate comprises a three-dimensional scaffold.

10. A non-viral transfection system, comprising:
    a substrate, wherein the substrate is three-dimensional poly($\alpha$-hydroxy ester) scaffold,
    a mineral coating on the surface of the substrate, wherein the mineral coating comprises a morphology selected from the group consisting of a spherulitic microstructure, a plate-like microstructure, a net-like microstructure, and combinations thereof;
    a polynucleotide-lipid complex bound to the mineral coating; and
    one or more cells, wherein the cell is selected from the group consisting of a pluripotent stem cell, a mesenchymal stem cell, and an umbilical vein endothelial cell.

* * * * *